(12) United States Patent
Laroya et al.

(10) Patent No.: US 10,548,706 B2
(45) Date of Patent: Feb. 4, 2020

(54) RETRIEVAL SNARE DEVICE AND METHOD

(71) Applicant: Volcano Corporation, San Diego, CA (US)

(72) Inventors: Gilbert Laroya, Santa Clara, CA (US); Paul Do, San Jose, CA (US); Eric Johnson, Woodside, CA (US)

(73) Assignee: VOLCANO CORPORATION, San Diego, CA (US)

( * ) Notice: Subject to any disclaimer, the term of this patent is extended or adjusted under 35 U.S.C. 154(b) by 601 days.

(21) Appl. No.: 13/739,828

(22) Filed: Jan. 11, 2013

(65) Prior Publication Data

US 2013/0184741 A1   Jul. 18, 2013

Related U.S. Application Data

(63) Continuation-in-part of application No. 13/475,819, filed on May 18, 2012, now Pat. No. 10,426,501.
(Continued)

(51) Int. Cl.
*A61B 17/22* (2006.01)
*A61F 2/01* (2006.01)
(Continued)

(52) U.S. Cl.
CPC .............. *A61F 2/01* (2013.01); *A61B 17/221* (2013.01); *A61B 2017/00358* (2013.01);
(Continued)

(58) Field of Classification Search
CPC ........ A61B 17/221; A61B 2017/00358; A61B 2017/2212; A61B 2017/2215; A61B 2017/2217; A61B 17/32056; A61F 2/01
(Continued)

(56) References Cited

U.S. PATENT DOCUMENTS 152,652 A   6/1874   Knowlton
407,971 A   7/1889   Siersdorfer
(Continued)

FOREIGN PATENT DOCUMENTS

CN   2635045 Y   8/2004
GB   1588072     4/1981
(Continued)

OTHER PUBLICATIONS

Johnson et al.; U.S. Appl. No. 14/575,935 entitled "Extended anchor endoluminal filter," filed Dec. 18, 2014.
(Continued)

*Primary Examiner* — Kathleen S Holwerda

(57) ABSTRACT

The present invention relates generally to devices and methods for retrieving or manipulating objects within a lumen. More specifically, embodiments of the invention relate to devices and methods for retrieving or manipulating medical devices from a body lumen. One embodiment of the present invention provides a novel and improved retrieval snare and method of fabricating and using the same. The snare includes a snare wire, having a distal end and a proximal end, for use in the human anatomy, such as but not limited to blood vessels, pulmonary airways, reproductive anatomy, gastrointestinal anatomy, and organs such as the kidneys or lungs. The device enables a user to capture a foreign object located within the human anatomy, grasp said object in a controlled manner, and retrieve and remove said object from the human anatomy.

22 Claims, 18 Drawing Sheets

Related U.S. Application Data

(60) Provisional application No. 61/586,683, filed on Jan. 13, 2012.

(51) Int. Cl.
*A61B 17/221* (2006.01)
*A61B 17/00* (2006.01)

(52) U.S. Cl.
CPC ............. *A61B 2017/2215* (2013.01); *A61B 2017/22035* (2013.01); *A61F 2002/011* (2013.01)

(58) Field of Classification Search
USPC .......................... 606/108, 113, 114, 127
See application file for complete search history.

(56) References Cited

U.S. PATENT DOCUMENTS

| | | | |
|---|---|---|---|
| 621,937 A | 3/1899 | Niemann | |
| 796,910 A | 8/1905 | Heman | |
| 1,950,378 A | 3/1934 | Andrews | |
| 2,163,324 A | 6/1939 | Reinhold | |
| 4,425,908 A | 1/1984 | Simon | |
| 4,619,246 A | 10/1986 | Molgaard-Nielsen et al. | |
| 4,909,789 A * | 3/1990 | Taguchi et al. ............... | 604/107 |
| 5,098,440 A | 3/1992 | Hillstead | |
| 5,234,458 A | 8/1993 | Metais | |
| 5,342,371 A * | 8/1994 | Welter et al. ................. | 606/113 |
| 5,370,657 A | 12/1994 | Irie | |
| 5,375,612 A | 12/1994 | Cottenceau et al. | |
| 5,601,595 A | 2/1997 | Smith | |
| 5,626,605 A | 5/1997 | Irie et al. | |
| 5,725,552 A | 3/1998 | Kotula et al. | |
| 5,814,064 A | 9/1998 | Daniel et al. | |
| RE36,057 E | 1/1999 | Martin | |
| 5,925,060 A | 7/1999 | Forber | |
| 5,944,738 A | 8/1999 | Amplatz et al. | |
| 6,053,925 A | 4/2000 | Barnhart | |
| 6,080,182 A | 6/2000 | Shaw et al. | |
| 6,099,534 A | 8/2000 | Bates et al. | |
| 6,106,476 A | 8/2000 | Coral et al. | |
| 6,171,327 B1 | 1/2001 | Daniel et al. | |
| 6,179,861 B1 * | 1/2001 | Khosravi ................... | A61F 2/01 606/194 |
| 6,231,581 B1 | 5/2001 | Shank et al. | |
| 6,346,116 B1 | 2/2002 | Brooks et al. | |
| 6,368,338 B1 | 4/2002 | Konya et al. | |
| 6,443,972 B1 | 9/2002 | Bosma et al. | |
| 6,458,145 B1 | 10/2002 | Ravenscroft et al. | |
| 6,468,301 B1 | 10/2002 | Amplatz et al. | |
| 6,485,502 B2 | 11/2002 | Don Michael et al. | |
| 6,530,939 B1 | 3/2003 | Hopkins et al. | |
| 6,537,297 B2 | 3/2003 | Tsugita et al. | |
| 6,544,279 B1 | 4/2003 | Hopkins et al. | |
| 6,554,849 B1 | 4/2003 | Jones et al. | |
| 6,610,077 B1 | 8/2003 | Hancock et al. | |
| 6,613,074 B1 | 9/2003 | Mitelberg et al. | |
| 6,626,915 B2 | 9/2003 | Leveillee | |
| 6,638,294 B1 | 10/2003 | Palmer | |
| 6,645,152 B1 | 11/2003 | Jung et al. | |
| 6,652,556 B1 | 11/2003 | VanTassel et al. | |
| 6,679,893 B1 * | 1/2004 | Tran ..................... | A61B 17/221 606/127 |
| 6,783,538 B2 | 8/2004 | McGuckin, Jr. et al. | |
| 6,824,545 B2 * | 11/2004 | Sepetka et al. ............... | 606/113 |
| 6,939,362 B2 | 9/2005 | Boyle et al. | |
| 6,958,074 B2 | 10/2005 | Russell | |
| 7,282,055 B2 | 10/2007 | Tsuruta | |
| 7,582,100 B2 | 9/2009 | Johnson et al. | |
| 7,645,292 B2 | 1/2010 | Porter | |
| 7,655,013 B2 | 2/2010 | Bieneman | |
| 7,695,484 B2 | 4/2010 | Wallace et al. | |
| 7,713,275 B2 | 5/2010 | Greenberg et al. | |
| 7,727,253 B2 * | 6/2010 | Ackerman ........... | A61B 17/221 606/114 |
| 7,753,918 B2 | 7/2010 | Hartley et al. | |
| 7,776,052 B2 | 8/2010 | Greenberg et al. | |
| 7,785,343 B2 | 8/2010 | Johnson et al. | |
| 7,789,892 B2 | 9/2010 | Johnson et al. | |
| 7,806,906 B2 | 10/2010 | Don Michael | |
| 7,854,747 B2 | 12/2010 | Johnson et al. | |
| 7,875,038 B2 | 1/2011 | Que et al. | |
| 8,057,506 B2 | 11/2011 | Gilson et al. | |
| 8,162,974 B2 | 4/2012 | Eskuri et al. | |
| 8,226,679 B2 | 7/2012 | Johnson et al. | |
| 8,801,748 B2 * | 8/2014 | Martin ................. | A61B 17/221 606/113 |
| 2001/0039432 A1 | 11/2001 | Whitcher et al. | |
| 2002/0022832 A1 * | 2/2002 | Mikus et al. .................. | 606/20 |
| 2002/0107541 A1 | 8/2002 | Vale et al. | |
| 2002/0120287 A1 | 8/2002 | Huter | |
| 2002/0183783 A1 | 12/2002 | Shadduck | |
| 2003/0040772 A1 | 2/2003 | Hyodoh et al. | |
| 2003/0097114 A1 | 5/2003 | Ouriel et al. | |
| 2003/0130684 A1 | 7/2003 | Brady et al. | |
| 2003/0171774 A1 | 9/2003 | Freudenthal et al. | |
| 2003/0171803 A1 | 9/2003 | Shimon | |
| 2003/0212429 A1 | 11/2003 | Keegan et al. | |
| 2004/0220608 A1 | 11/2004 | D'Aquanni et al. | |
| 2004/0243174 A1 * | 12/2004 | Ackerman ........... | A61B 17/221 606/200 |
| 2005/0043756 A1 * | 2/2005 | Lavelle ................ | A61B 17/221 606/200 |
| 2005/0107822 A1 | 5/2005 | WasDyke | |
| 2005/0154416 A1 | 7/2005 | Herweck et al. | |
| 2006/0020286 A1 | 1/2006 | Niermann | |
| 2006/0069405 A1 | 3/2006 | Schaeffer et al. | |
| 2006/0100658 A1 | 5/2006 | Obana et al. | |
| 2006/0149312 A1 * | 7/2006 | Arguello ................. | A61F 2/013 606/200 |
| 2006/0241677 A1 | 10/2006 | Johnson et al. | |
| 2006/0241678 A1 | 10/2006 | Johnson et al. | |
| 2006/0241679 A1 | 10/2006 | Johnson et al. | |
| 2007/0123932 A1 | 5/2007 | Gray et al. | |
| 2007/0239141 A1 * | 10/2007 | Hartley et al. .................... | 606/1 |
| 2008/0004687 A1 | 1/2008 | Barbut et al. | |
| 2008/0021497 A1 | 1/2008 | Johnson et al. | |
| 2008/0033482 A1 | 2/2008 | Kusleika | |
| 2008/0086149 A1 | 4/2008 | Diamant et al. | |
| 2008/0147111 A1 | 6/2008 | Johnson et al. | |
| 2009/0326575 A1 | 12/2009 | Galdonik et al. | |
| 2010/0185231 A1 | 7/2010 | Lashinski | |
| 2010/0191276 A1 | 7/2010 | Lashinski | |
| 2010/0268265 A1 | 10/2010 | Krolik et al. | |
| 2010/0318115 A1 | 12/2010 | Chanduszko et al. | |
| 2010/0324590 A1 | 12/2010 | Johnson et al. | |
| 2011/0034718 A1 | 2/2011 | Nakazawa | |
| 2011/0264106 A1 * | 10/2011 | Taube ............... | A61B 17/22031 606/113 |
| 2011/0282379 A1 | 11/2011 | Lee et al. | |
| 2012/0010650 A1 | 1/2012 | Sos | |
| 2012/0050165 A1 | 3/2012 | Kim | |
| 2012/0179196 A1 | 7/2012 | Johnson et al. | |
| 2013/0012981 A1 | 1/2013 | Johnson et al. | |
| 2013/0035715 A1 | 2/2013 | Johnson et al. | |
| 2015/0164630 A1 | 6/2015 | Johnson et al. | |

FOREIGN PATENT DOCUMENTS

| | | |
|---|---|---|
| JP | 10-509623 | 9/1998 |
| JP | 2012500054 A | 1/2012 |
| WO | WO 02/02162 A2 | 1/2002 |
| WO | WO 2005/102211 A1 | 11/2005 |
| WO | WO 2006/034233 A1 | 3/2006 |
| WO | WO 2009/086482 A1 | 7/2009 |
| WO | WO 2012/003369 A2 | 1/2012 |
| WO | WO 2012/031149 A1 | 3/2012 |

(56) References Cited

FOREIGN PATENT DOCUMENTS

| | | |
|---|---|---|
| WO | WO 2012092377 A1 | 7/2012 |
| WO | WO 2012/118696 A1 | 9/2012 |

OTHER PUBLICATIONS

Johnson et al.; U.S. Appl. No. 14/578,087 entitled "Devices and methods for controlled endoluminal filter deployment," filed Dec. 19, 2015.

Johnson et al.; U.S. Appl. No. 14/581,638 entitled "Treatment structure and methods of use," filed Dec. 23, 2014.

Johnson et al.; U.S. Appl. No. 13/919,630 entitled "Methods for Maintaining a Filtering Device Within a Lumen," filed Jun. 17, 2013.

Johnson et al.; U.S. Appl. No. 13/919,658 entitled "Biodegradable Implant Device," filed Jun. 17, 2013.

Johnson et al.; U.S. Appl. No. 13/919,680 entitled "Endoluminal Filter," filed Jun. 17, 2013.

Johnson et al.; U.S. Appl. No. 13/919,718 entitled "Endoluminal Filter," filed Jun. 17, 2013.

Johnson et al.; U.S. Appl. No. 13/931,462 entitled "Retrievable Endoluminal Filter" filed Jun. 28, 2013.

Johnson et al.; U.S. Appl. No. 13/931,408 entitled "Endoluminal Filter," filed Jun. 28, 2013.

Johnson et al.; U.S. Appl. No. 13/931,334 entitled "Filter Delivery Methods," filed Jun. 28, 2013.

Johnson et al.; U.S. Appl. No. 13/931,256 entitled "Methods for Maintaining a Filtering Device Within a Lumen," filed Jun. 28, 2013.

Laroya et al.; U.S. Appl. No. 14/458,168 entitled "Retrieval Snare Device and Method," filed Aug. 12, 2014.

Johnson et al.; U.S. Appl. No. 14/372,180 entitled "Endoluminal Filter With Fixation," filed Jul. 14, 2014.

Kahraman et al.; The Diameters of the Aorta and Its Major Branches in Patients with Isolated Coronary Artery Ectasia; Tex Heart Inst J.; vol. 33, No. 4: pp. 463R468; (year of publication is sufficiently earlier than the effective U.S. filed and any foreign priority date) 2006.

Millward, Steven F.; Temporary and retrievable inferior vena cava filters; JVIR; vol. 9; No. 3; pp. 381-387, May/Jun. 1998.

Siskin, Gary P.; Inferior Vena Cava Filters; eMedicine; Sep. 7, 2004.

Streiff, Michael B.; Vena caval filters; a comprehensive review; Blood; vol. 95; No. 12; pp. 3669-3677; Jun. 15, 2000.

Laroya et al.; U.S. Appl. No. 13/475,819 entitled "Retrieval Snare Device and Method," filed May 18, 2012.

Johnson et al.; U.S. Appl. No. 13/472,417 entitled "Distal Protection Filter," filed May 15, 2012.

Johnson et al.; U.S. Appl. No. 13/791,464 entitled "Coated endoluminal filters," filed Mar. 8, 2013.

Johnson et al.; U.S. Appl. No. 13/791,557 entitled "Methods for providing protection during procedures in the vasculature," filed Mar. 8, 2013.

Johnson et al.; U.S. Appl. No. 13/791,610 entitled "Spiral shaped filter," filed Mar. 8, 2013.

Johnson et al.; U.S. Appl. No. 13/802,657 entitled "Distal protection device," filed Mar. 13, 2013.

\* cited by examiner

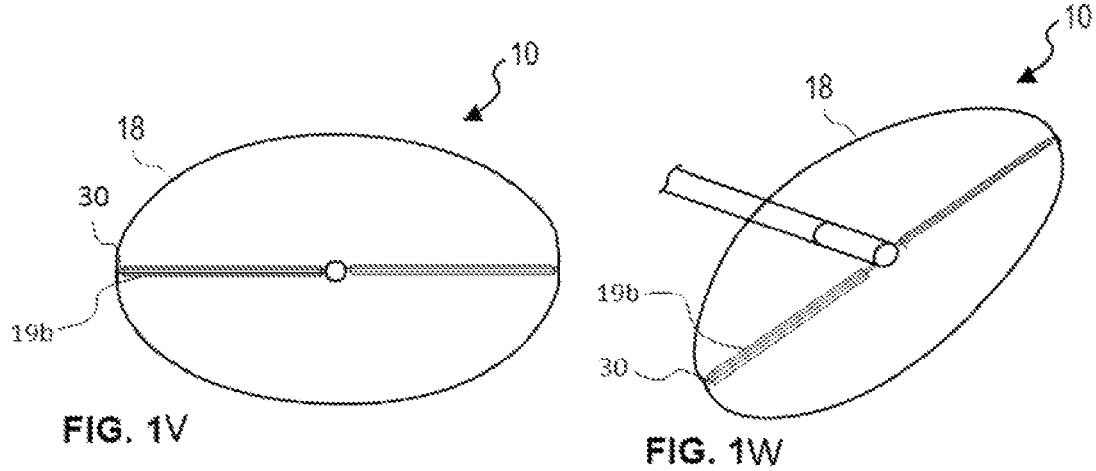
FIG. 1V
FIG. 1W
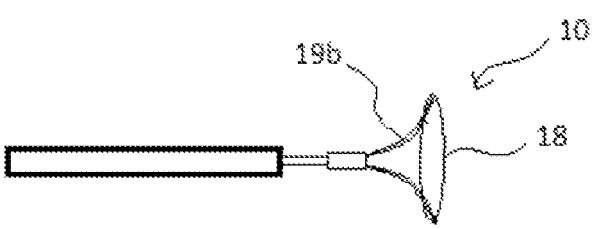
FIG. 1X

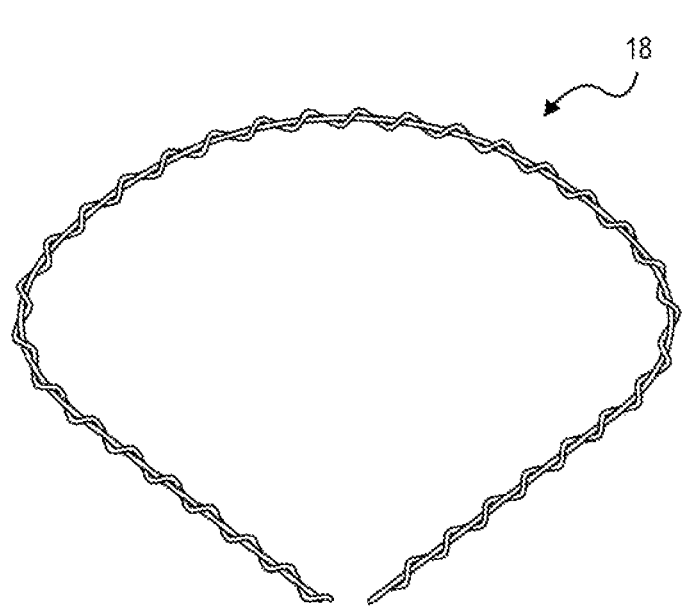
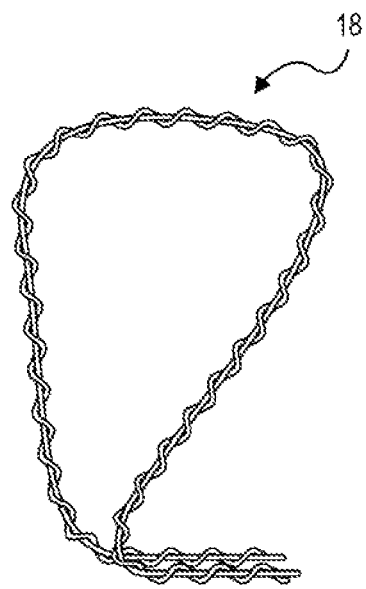
FIG. 2A
FIG. 2B
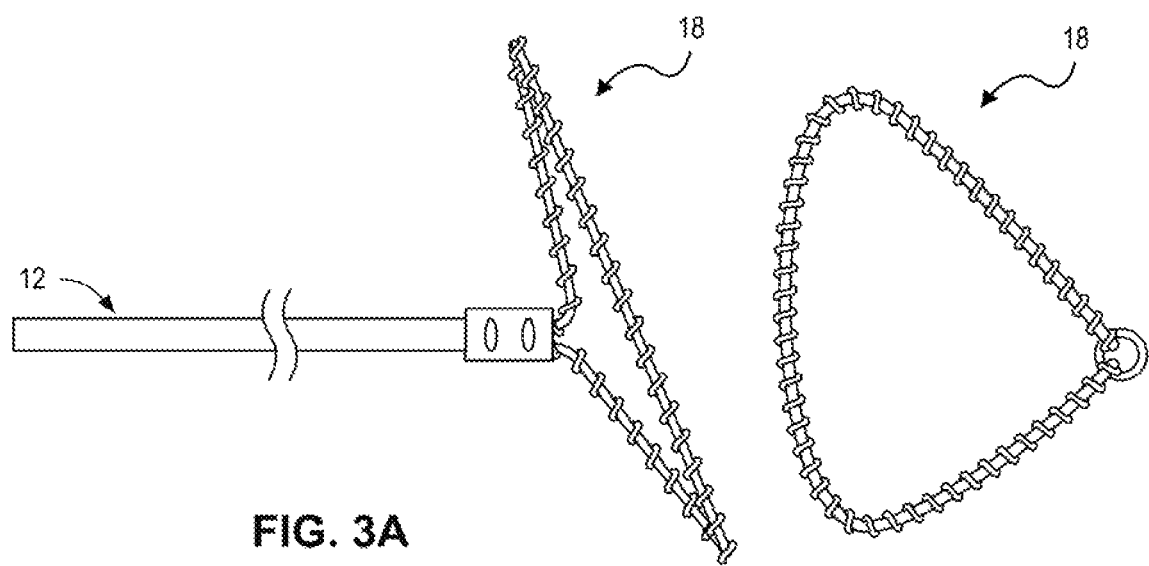
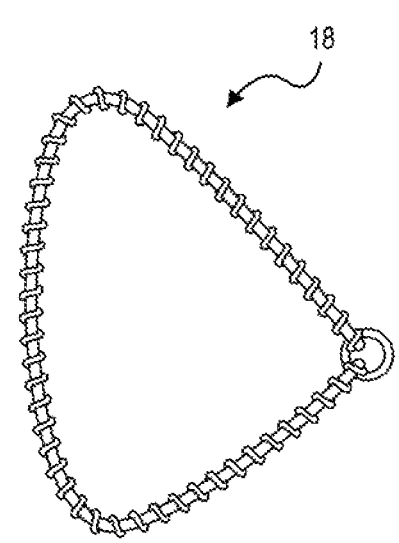
FIG. 3A
FIG. 3B

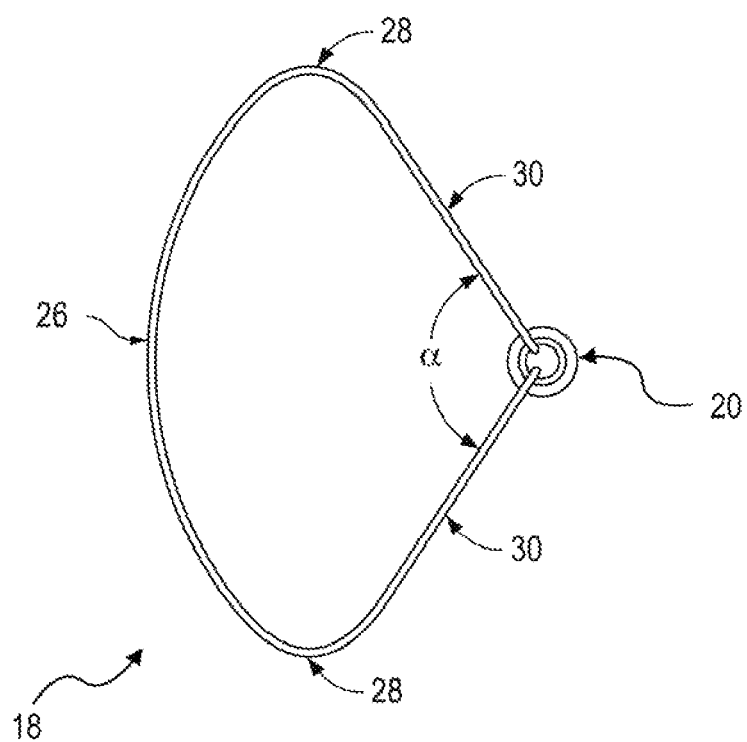
FIG. 4
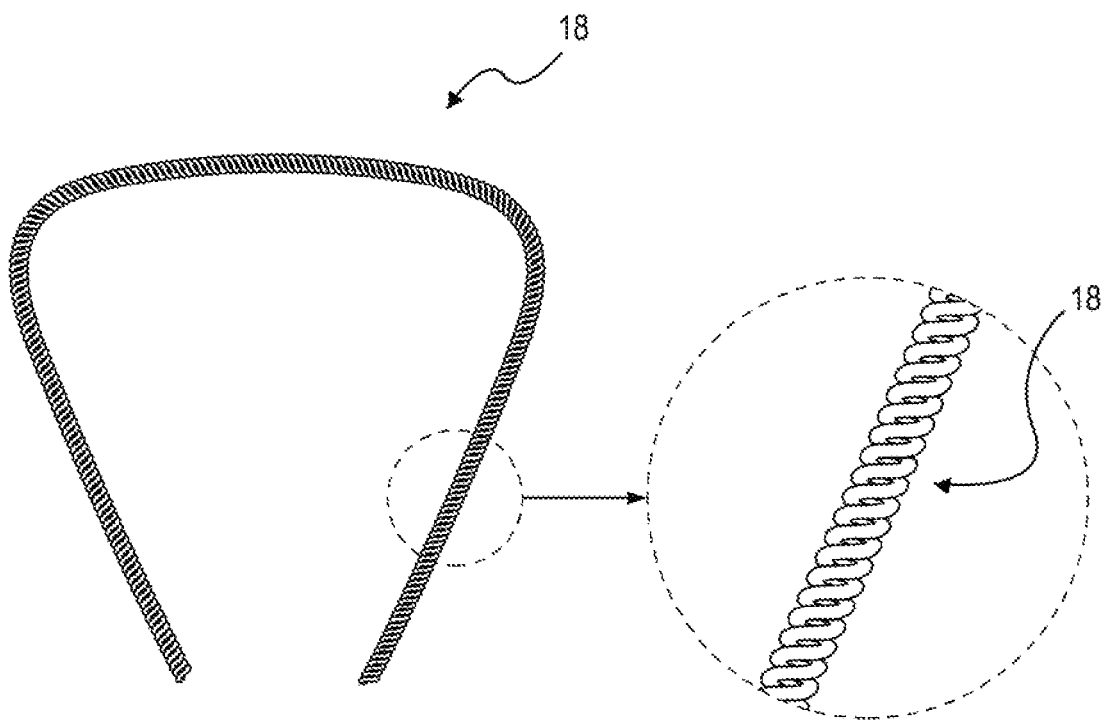
FIG. 5A FIG. 5B

RETRIEVAL SNARE DEVICE AND METHOD

CROSS REFERENCE TO RELATED APPLICATIONS

This application is a continuation-in-part of U.S. application Ser. No. 13/475,819, filed May 18, 2012, and entitled "Retrieval Snare Device and Method," which claims the benefit of U.S. Provisional Application No. 61/586,683, filed Jan. 13, 2012, and entitled "Retrieval Snare Device and Method," which is hereby incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

The following patents and patent applications are herein incorporated by reference in their entirety: U.S. patent application Ser. No. 11/969,827 titled, "ENDOLUMINAL FILTER WITH FIXATION" filed on Jan. 4, 2009.

FIELD

Embodiments of the invention relate generally to devices and methods for retrieving or manipulating objects within a lumen. More specifically, embodiments of the invention relate to devices and methods for retrieving or manipulating medical devices from a body lumen.

BACKGROUND

Embolic protection is utilized throughout the vasculature to prevent the potentially fatal passage of embolic material in the bloodstream to smaller vessels where it can obstruct blood flow. The dislodgement of embolic material is often associated with procedures which open blood vessels to restore natural blood flow such as stenting, angioplasty, arthrectomy, endarterectomy or thrombectomy. Used as an adjunct to these procedures, embolic protection devices trap debris and provide a means for removal for the body.

One widely used embolic protection application is the placement of filtration means in the vena cava. Vena cava filters (VCF) prevent the passage of thrombus from the deep veins of the legs into the blood stream and ultimately to the lungs. This condition is known as deep vein thrombosis (DVT), which can cause a potentially fatal condition known as pulmonary embolism (PE).

The next advancement in filters added the element of recoverability. Retrievable filters were designed to allow removal from the patient subsequent to initial placement. These filters can incorporate retrieval features that can be grasped and/or secured by a retrieval device, such as a snare based retrieval device. Grasping the retrieval feature using a snare generally requires the user to manipulate the snare over the retrieval feature, which can be difficult due to a variety of factors, such as retrieval feature geometry and location within the lumen, the structure and properties of the snare, and ability to visualize the retrieval feature and/or snare using a real-time visualization technique such as fluoroscopy.

Accordingly, it would be desirable to have an improved retrieval device that would facilitate engagement with a retrieval feature on a device making retrieval and/or manipulation of the device easier and faster to complete.

SUMMARY OF THE DISCLOSURE

The present invention relates generally to devices and methods for retrieving or manipulating objects within a lumen. More specifically, embodiments of the invention relate to devices and methods for retrieving or manipulating medical devices from a body lumen.

One embodiment of the present invention provides a novel and improved retrieval snare and method of fabricating and using the same. The snare includes a snare wire, having a distal end and a proximal end, for use in the human anatomy, such as but not limited to blood vessels, pulmonary airways, reproductive anatomy, gastrointestinal anatomy, and organs such as the bladder, kidneys or lungs. The device enables a user to capture a foreign object located within the human anatomy, grasp said object in a controlled manner, and retrieve and remove said object from the human anatomy. Examples of foreign objects which might be removed from the human anatomy include implants such as stents, guidewires, leads, sheaths, filters, and valves, and organic objects such as kidney stones or calcified emboli. Other areas where embodiments of the snare can be used include, for example, removal and/or repositioning of distal protection devices that are used in a variety of medical procedures such as carotid stenting and percutaneous aortic valve replacement; and abdominal aortic aneurysm and thoracic aortic aneurysm devices. For example, a snare can be used to capture a vena cava filter and pull it into a retrieval sheath for removal from the patient. The snare is advanced through one or more retrieval sheaths, up to the site of a deployed filter. The snare is then deployed into the vessel, and engaged with the filter. Finally, the snare is held under tension while the sheath is advanced over said filter, collapsing it into the ID of said sheath. Another example is the use of a snare to grasp and extract loose kidney stones from a patient's kidneys. The snare is advanced through one or more sheaths, up to the site of the loose kidney stone. The snare is then deployed and engaged with the stone. Next, the snare is pulled into the sheath, drawing the stone into the distal ID of said sheath.

In some embodiments, a device for retrieving an object from a lumen is provided. The device includes a sheath configured to fit within the lumen, the sheath having a proximal end and a distal end. A snare can be disposed within the sheath. The snare can have a shaft with a longitudinal axis, a proximal end and a distal end and a plurality of loop elements in connection with the distal end of the shaft. The plurality of loop elements can have a collapsed configuration within the sheath and at least one deployed configuration outside the sheath. The plurality of loop elements can be configured to be deployed through an opening at the distal end of the sheath. The at least one deployed configuration can include a fully deployed configuration in which the plurality of loop elements are deployed in a propeller-like configuration.

In some embodiments, the first sheath includes a flexible distal tip portion that is configured to invert when the object is withdrawn into the sheath.

In some embodiments, a plurality of sheaths includes flexible distal tip portions that are configured to invert when the object is withdrawn into the sheaths.

In some embodiments, the plurality of loop elements in the fully deployed configuration are angled less than 90 degrees with respect to the longitudinal axis of the shaft such that the plurality of loop elements has an axial reach both proximal and distal the distal end of the shaft.

In some embodiments, each of the plurality of loop elements includes at least one shape memory wire and one radiopaque wire.

In some embodiments, the shape memory wire is made of a nickel titanium alloy and the radiopaque wire is made of platinum.

In some embodiments, the loop elements in the fully deployed configuration are arranged to form a circle geometry when viewed along the longitudinal axis.

In some embodiments, the object being retrieved by the device is a filter having a retrieval element and a support member, and wherein the axial reach of the loop elements in the fully deployed configuration is less than the distance between the retrieval element and the support member.

In some embodiments, the proximal portion of the sheath and the proximal portion of the shaft are connected with a snap fitting.

In some embodiments, the proximal portion of the outer sheath and the proximal portion of the inner sheath are connected with a snap fitting.

In some embodiments, the device further includes an outer sheath, wherein the sheath is disposed within the outer sheath.

In some embodiments, the outer sheath has greater column strength than the inner sheath.

In some embodiments, the loop elements have a plurality of deployment configurations, and wherein the proximal portion of the shaft includes a plurality of indicators that correspond to the plurality of deployment configurations.

In some embodiments, the plurality of indicators includes a plurality of detents.

In some embodiments, the proximal portion of the sheath includes a first tactile identifier and the proximal portion of the shaft includes a second tactile identifier, wherein the first tactile identifier is different from the second tactile identifier.

In some embodiments, the at least one deployed configuration includes an initial deployed configuration in which the plurality of loop elements are deployed substantially transversely with respect to the longitudinal axis.

In some embodiments, the plurality of loop elements is deployed in a clover leaf configuration in the initial deployed configuration.

In some embodiments, the at least one deployed configuration includes an intermediate deployed configuration in which the plurality of loop elements are deployed substantially axially with respect to the longitudinal axis.

In some embodiments, a method for capturing an object in a lumen defined by a lumen wall is provided. The method includes advancing a sheath within the lumen, the sheath having a proximal end and a distal end, until the distal end of the sheath is proximal the object; deploying a plurality of loop elements of a snare out of the distal end of the sheath in a propeller-like configuration; and capturing a portion of the object with at least one of the plurality of loop elements.

In some embodiments, the method further includes withdrawing the loop elements in a proximal direction to engage the portion of the object.

In some embodiments, the method further includes rotating the loop elements to engage the portion of the object.

In some embodiments, the method further includes retracting the portion of the object within the sheath.

In some embodiments, the method further includes advancing an outer sheath over the object.

In some embodiments, the method further includes advancing the snare to a full deployment detent on the snare.

In some embodiments, the method further includes visualizing the snare in the lumen using fluoroscopy.

In some embodiments, the method further includes decoupling a snap fitting holding together the sheath and the snare.

In some embodiments, the method further includes decoupling a snap fitting holding together the outer sheath and the inner sheath.

In some embodiments, a device for retrieving an object from a lumen is provided. The device can include a sheath configured to fit within the lumen, the sheath having a proximal end, a distal end and a radiopaque marker offset from the distal end. A snare can be disposed within the sheath, the snare having a shaft with a longitudinal axis, a proximal end and a distal end and a plurality of loop elements in connection with the distal end of the shaft. The plurality of loop elements can have a collapsed configuration within the sheath and at least one deployed configuration outside the sheath. The plurality of loop elements can be configured to be deployed through an opening at the distal end of the sheath. At least one deployed configuration can include an initial deployed configuration in which the plurality of loop elements is deployed substantially transversely with respect to the longitudinal axis.

In some embodiments, the plurality of loop elements are deployed in a clover leaf configuration in the initial deployed configuration.

In some embodiments, the plurality of loop elements are deployed in an elliptical or oblong configuration in the fully deployed configuration.

In some embodiments, the at least one deployed configuration includes a fully deployed configuration in which the plurality of loop elements are deployed in substantially circular configuration.

In some embodiments, the radiopaque marker is offset about 3 to 5 mm from the distal end of the sheath.

In some embodiments, a specific radiopaque marker pattern is disposed on each of the loop elements to enable visual differentiation of each loop element fluoroscopically. For example, each loop element can have a different number of radiopaque markers.

In some embodiments, a method for capturing an object in a lumen defined by a lumen wall is provided. The method includes advancing a sheath within the lumen, the sheath having a proximal end and a distal end, until the distal end of the sheath is proximal the object; deploying a plurality of loop elements of a snare out of the distal end of the sheath until the loop elements achieve substantially full apposition with the circumference of the lumen wall; and capturing a portion of the object with at least one of the plurality of loop elements.

In some embodiments, the method further includes aligning a radiopaque marker offset from the distal end of the sheath with a radiopaque feature of the object.

In some embodiments, the radiopaque feature of the object is a retrieval element.

In some embodiments, a device for retrieving an object from a lumen defined by a lumen wall is provided. The device can include a sheath configured to fit within the lumen, the sheath having a proximal end and a distal end; and a snare slidably disposed within the sheath, the snare having a shaft with a longitudinal axis, a proximal end and a distal end and a plurality of loop elements in connection with the distal end of the shaft, wherein each of the plurality of loop element has a proximal portion and a distal portion, wherein the plurality of loop elements has a collapsed configuration within the sheath and at least one deployed configuration outside the sheath, wherein the plurality of loop elements are configured to be deployed through an opening at the distal end of the sheath, wherein the at least one deployed configuration includes a fully deployed configuration in which the plurality of loop elements are deployed such that the distal portions of the loop elements are arranged in a substantially continuous, circumferential, planar and oblong configuration that is transverse to the longitudinal axis.

In some embodiments, the sheath includes a flexible distal tip portion that is configured to invert when the object is withdrawn into the sheath.

In some embodiments, the plurality of loop elements in the fully deployed configuration are angled less than 90 degrees with respect to the longitudinal axis of the shaft such that the plurality of loop elements has an axial reach both proximal and distal the distal end of the shaft.

In some embodiments, each of the plurality of loop elements includes at least one shape memory wire and one radiopaque wire. In some embodiments, the shape memory wire is made of a nickel titanium alloy and the radiopaque wire is made of platinum.

In some embodiments, the proximal portions of the plurality of loop elements comprise spoke portions that are secured together with a flexible sleeve.

In some embodiments, the object is a filter having a retrieval element and a support member, and wherein the axial reach of the loop elements in the fully deployed configuration is less than the distance between the retrieval element and the support member.

In some embodiments, the proximal portion of the sheath and the proximal portion of the shaft are connected with a snap fitting.

In some embodiments, the device further includes an outer sheath, wherein the sheath is disposed within the outer sheath.

In some embodiments, the outer sheath has greater column strength than the sheath.

In some embodiments, the loop elements have a plurality of deployment configurations, and wherein the proximal portion of the shaft includes a plurality of indicators that correspond to the plurality of deployment configurations. In some embodiments, the plurality of indicators comprise a plurality of detents. In some embodiments, the proximal portion of the sheath includes a first tactile identifier and the proximal portion of the shaft includes a second tactile identifier, wherein the first tactile identifier is different from the second tactile identifier.

In some embodiments, the at least one deployed configuration includes an initial deployed configuration in which the plurality of loop elements are deployed substantially axially with respect to the longitudinal axis.

In some embodiments, the distal portions of the plurality of loop elements in the fully deployed configuration are configured to achieve complete circumferential apposition with the lumen wall. In some embodiments, the lumen wall can define a lumen that is oblong or circular or that changes between oblong and circular.

In some embodiments, the at least one deployed configuration includes an intermediate deployed configuration in which the plurality of loop elements are deployed substantially transversely with respect to the longitudinal axis.

In some embodiments, a device for retrieving an object from a lumen is provided. The device can include a sheath configured to fit within the lumen, the sheath having a proximal end, a distal end and a radiopaque marker offset from the distal end; and a snare disposed within the sheath, the snare having a shaft with a longitudinal axis, a proximal end and a distal end and a plurality of loop elements in connection with the distal end of the shaft, wherein the plurality of loop elements has a collapsed configuration within the sheath and at least one deployed configuration outside the sheath, wherein the plurality of loop elements are configured to be deployed through an opening at the distal end of the sheath, wherein the at least one deployed configuration includes an initial deployed configuration in which the plurality of loop elements are deployed substantially transversely with respect to the longitudinal axis.

In some embodiments, the at least one deployed configuration includes a fully deployed configuration in which the plurality of loop elements are deployed in substantially circular configuration.

In some embodiments, the radiopaque marker is offset about 3 to 5 mm from the distal end of the sheath.

In some embodiments, the at least one deployed configuration includes a fully deployed configuration in which the plurality of loop elements are deployed in substantially oblong configuration.

In some embodiments, the plurality of loop elements each includes a loop collapse facilitator.

In some embodiments, the plurality of loop elements are secured together with sleeves.

In some embodiments, a method for capturing an object in a lumen defined by a lumen wall is provided. The method can include advancing a sheath within the lumen, the sheath having a proximal end and a distal end, until the distal end of the sheath is proximal the object; deploying a plurality of loop elements of a snare out of the distal end of the sheath until the loop elements achieve substantially full apposition with the circumference of the lumen wall; and capturing a portion of the object proximate to the lumen wall with at least one of the plurality of loop elements.

In some embodiments, the method further includes aligning a radiopaque marker offset from the distal end of the sheath with a radiopaque feature of the object.

In some embodiments, the radiopaque feature of the object is a retrieval element.

In some embodiments, the method further includes advancing the distal end of the sheath over the captured object.

In some embodiments, the distal end of the sheath inverts as the sheath is advanced over the captured object.

In some embodiments, a method for capturing an object in a lumen defined by a lumen wall is provided. The method includes advancing a sheath within the lumen, the sheath having a proximal end and a distal end, until the distal end of the sheath is proximal the object; determining the position of the object within the lumen; deploying a plurality of loop elements of a snare out of the distal end of the sheath to one of a plurality of predetermined loop element deployment configurations based on the determination of the position of the object; and capturing a portion of the object with at least one of the plurality of loop elements.

In some embodiments, the plurality of loop elements are deployed to the predetermined loop element deployment configuration using a deployment indicator.

In some embodiments, the method further includes advancing an inner sheath disposed with the sheath over a portion of the object and advancing the sheath over the entire object.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1D and 1E illustrate an initial deployment stage of the loop elements, while FIG. 1F illustrates an intermediate deployment stage of the loop elements.

FIGS. 1V-1X illustrate another snare embodiment having two loop elements that are fastened together at the swage and attached together with sleeves.

FIG. 2A is an end view of an embodiment of a single loop element, using a single nitinol wire wrapped with a single radiopaque platinum wire.

FIG. 2B is a perspective view of the single loop element shown in FIG. 2A.

FIG. 3A is a side view of another embodiment of a single loop on the end of a snare device, to illustrate the relative geometry of the loop elements.

FIG. 3B is an end view of the single loop shown in FIG. 3A.

FIG. 4 is an end view of a loop element and a hypo tube, to illustrate the D shape or pie shape geometry of the loop element features.

FIG. 5A is an end view of an embodiment of a single loop element, using a plurality of wires which are twisted together to form a strand.

FIG. 5B is a close up view of a portion of the single loop element strand shown in FIG. 5A.

DETAILED DESCRIPTION

Figure 1A:
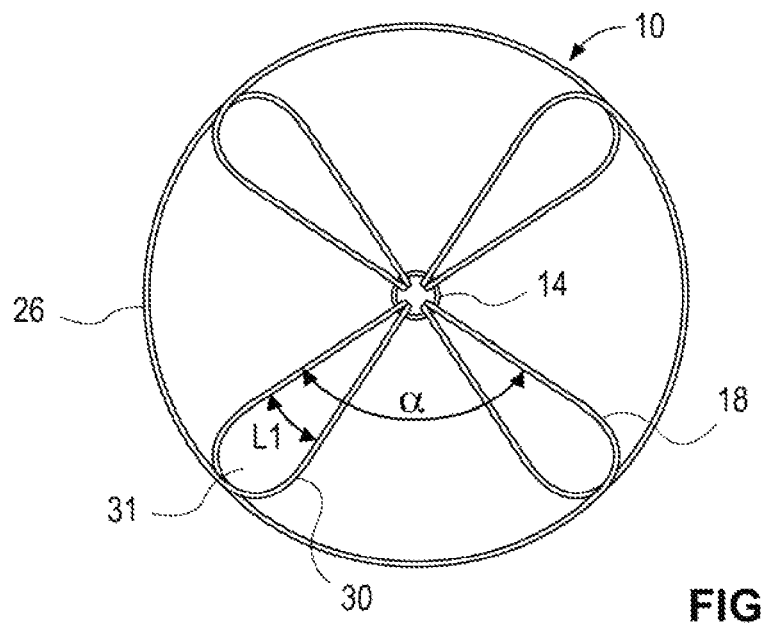
FIG. 1A is an axial view of the distal end of one embodiment of the snare device, showing the loop elements which substantially form a complete circle about the axis of the shaft. The edges of each loop overlap adjacent loops to ensure a substantially continuous circular pattern.
Figure 1B:
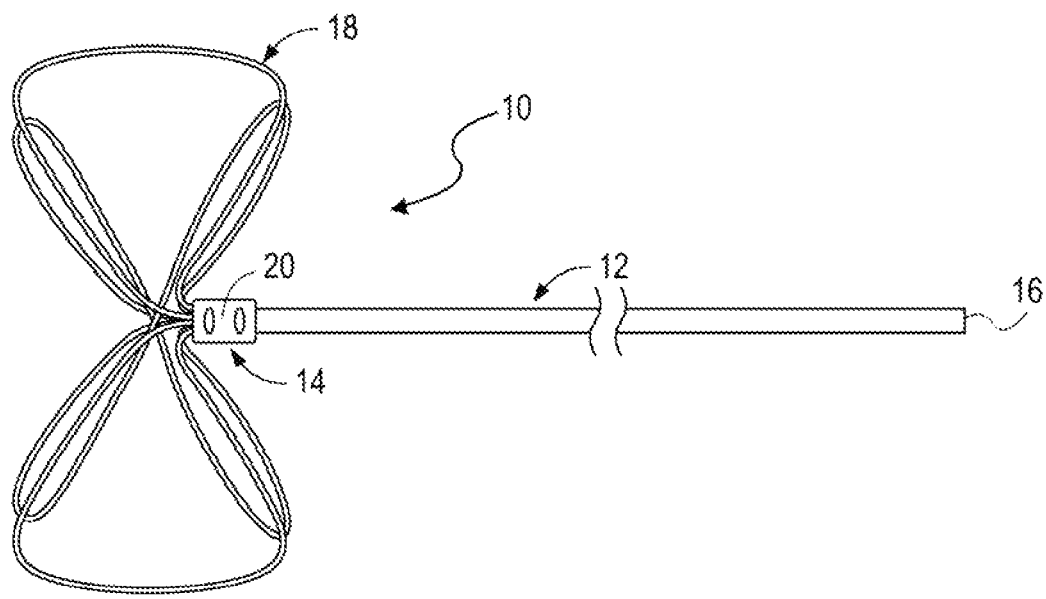
FIG. 1B is a side perspective view of the snare device shown in FIG. 1A, showing the loop elements such that the plurality of loop elements has an axial reach both proximal and distal the distal end of the shaft.

As illustrated in FIGS. 1A and 1B, an embodiment of a retrieval device 10, such as a snare, includes a primary or main shaft 12, having a distal end 14 and a proximal end 16. At the distal end 14 of the shaft 12 is a plurality of loop elements 18. In some embodiments, the device 10 can typically have at least two loop elements 18, but can have three or more loop elements 18. These loop elements 18 are attached proximally to the distal end 14 of the shaft 12 via a hypo tube component 20, and can be free and independent at their distal-most ends. In other embodiments, the distal ends of the loop elements 18 can be fastened or connected to adjacent loop elements using, for example, loop connectors, as described in more detail below. The loops 18 can be of a polymeric or metallic material, and are typically radiopaque and flexible.

The loop elements 18 can have a region of overlap 31, with a span L1, between the adjacent loop elements. In some embodiments, L1 can be less than about 5, 10, 15, 20, 25, 30, 35, 40 or 45 degrees. In some embodiments, L1 can be between about 0 to 45 degrees, or about 0 to 15 degrees. The span of radial or circumferential coverage by each loop element 18 can be defined by the angle α between the two spoke elements 30 of the loop element 18, as shown in FIG. 1A and FIG. 4. In some embodiments, angle α depends on the number of loop elements 18 and the amount of loop element overlap, L1. For example, in some embodiments, angle α can be determined approximately by dividing 360 degrees by the number of loop elements and then adding the amount of overlap, L1. Thus, for a four loop element snare embodiment with 10 degrees of overlap between each loop element, angle α equals approximately 100 degrees. For a two loop element snare embodiment with 10 degrees of overlap, angle α equals about 190 degrees. In other embodiments, the radial or circumferential coverage of the loop elements can be different while still providing complete radial or circumferential coverage. For example, in a four loop element embodiment with 10 degrees overlap, two loop elements can have an angle α of about 130 degrees while the other two loop elements can have an angle α of about 70 degrees.

Figure 1C:
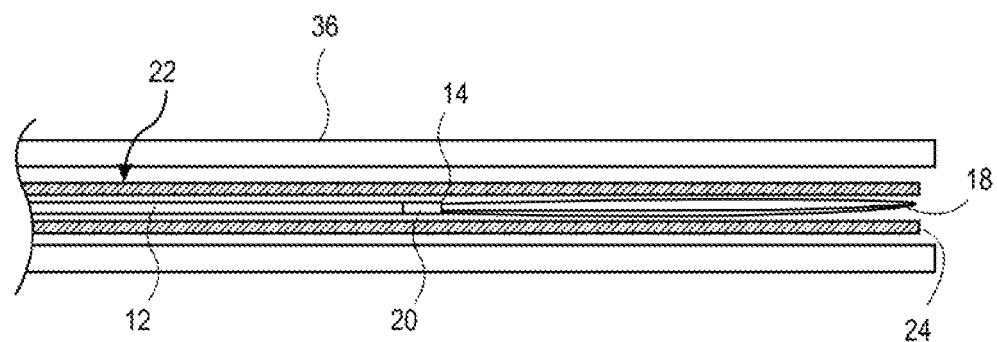
FIG. 1C is a side cross-sectional view of a stowed snare within both an outer sheath and an inner sheath.

The shape and flexibility of the loop elements 18 allows them to collapse and/or fold down easily into, for example, a 7 Fr or smaller sheath catheter 22 during loading of the device 10 into the sheath 22 and/or during deployment of the device 10 from the sheath 22 and retraction of the device 10 into the sheath 22, as illustrated in FIG. 1C. In some embodiments, an additional outer sheath 36 can be used to provide additional column strength. In some embodiments, the outer sheath 36 can be a braided sheath, while the inner sheath 22 can be a coiled sheath, which can be more flexible that the braided sheath. The outer sheath 36 can be used with any of the embodiments disclosed herein.

Figure 1D:
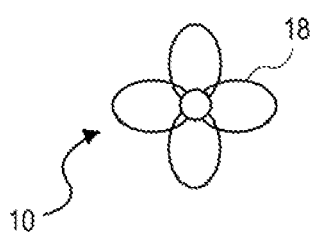
FIGS. 1D-1F illustrate the various deployment stages of the loop elements of one embodiment of the snare.
Figure 1E:
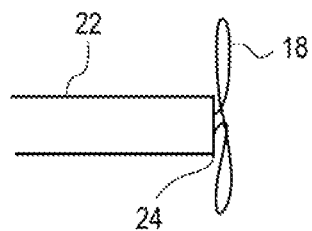
Figure 1F:
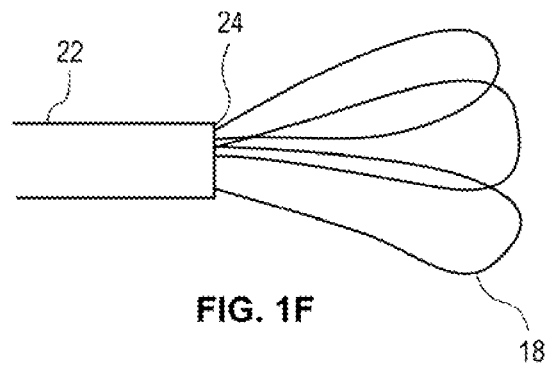
Figure 1G:
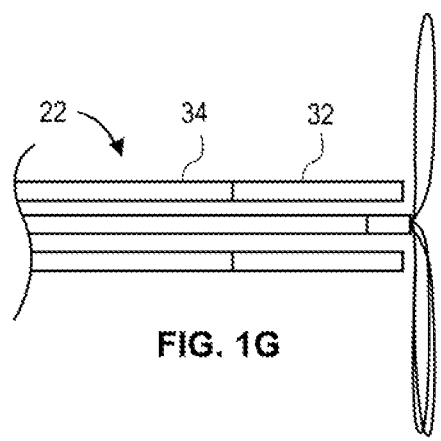
FIGS. 1G and 1H illustrate the flexible distal tip portion of the sheath with a deployed snare (FIG. 1G) and a partially stowed snare (FIG. 1H).
Figure 1H:
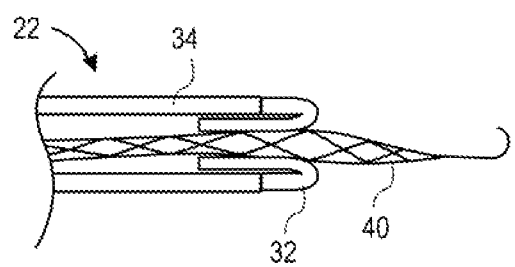

In some embodiments, as illustrated in FIGS. 1G and 1H, the sheath 22, which can be used in a single sheath embodiment or as an inner sheath in a double sheath embodiment, can have a soft, flexible and elastic distal tip portion 32 that can expand over a foreign object, such as a filter 40, that is being pulled into the sheath 22. In addition, the flexible distal tip portion 32 can evert when the foreign object and/or deployed loop elements 18 are retracted back into the sheath 22. When the flexible distal tip portion 32 inverts, it can form a ramp-like structure that facilitates the retraction of the filter 40 and the loop elements 18 back into the sheath 22. The main portion 34 of the sheath 22 can have stiffer column strength than the flexible distal tip portion 32 in order to tolerate the relatively high levels of force that can be generated while pulling out embedded filters with the device 10. In some embodiments, as mentioned above, an outer sheath can be used to provide additional column strength if needed.

In some embodiments, the distal tip portion 32 of the sheath 22 can be radiopaque and/or include a radiopaque marker. For example, in some embodiments, the polymer forming the distal tip portion 32 can be doped with radiopaque elements or compounds, such as barium, tantalum, tungsten, palladium, platinum or iridium based compounds or elements. Alternatively or in addition to the radiopaque doping, a single or plurality of radiopaque markers, such as a radiopaque marker band made of the radiopaque elements or compounds described herein, can be incorporated into the distal tip portion 32. In some embodiments, the radiopaque marker band can be offset approximately 1-10 mm, or about 3-mm from the distal end of the sheath 22, so as to not interfere with the elasticity and eversion of the distal tip portion 32 during the capture process. The radiopaque doping and/or marker allow the operator to visualize the location of the distal tip portion 32 of the sheath 22 during insertion, advancement, and positioning of the sheath 22 near the foreign object within the lumen. This allows the operator to accurately and precisely advance and position the tip of sheath 22 to the foreign object. In some embodiments where an outer sheath is combined with the retrieval sheath, each sheath can employ different radiopaque marker patterns to allow the operator to differentiate between the two sheaths fluoroscopically.

In addition, the marker offset can also function as an alignment feature which aids the operator in positioning the distal end of the sheath 22 in the proper location relative to the foreign object to be retrieved. For example, the foreign object can be a filter 40 with a frame 52, a plurality of anchors 50 on the frame 40 and a retrieval element 42 as illustrated in FIGS. 16-19. In some embodiments, deployment of the loop elements 18 is ideally distal the retrieval element 42 but proximal the anchor 50 closest to the retrieval element 42, which can be achieved be lining up the marker band 54 with an element or feature on the filter 40, such as the retrieval element 42, for example. The distance d between the retrieval element 42 and the anchor 50 can serve as a design constraint for loop element 18 deployments, where the loop elements 18 can be designed to deploy with an axial reach of less than the distance d between the retrieval element 42 and the anchor 50 or other feature on the filter 40. FIGS. 16-19 are more fully described below.

In some embodiments, the shaft 12 is straight and can be made of polymeric or metallic material, for example. The shaft 12 can be made of a solid design such as a wire, but can alternatively be hollow to facilitate passage of secondary devices through a lumen in the shaft 12. The shaft 12 can be of a single wire or element, but can also be constructed of a plurality of wires or elements which can be braided, twisted or stranded into a single shaft 12. The shaft 12 provides a means by which the user can advance, manipulate, and retract the distal end 14 of the device to capture and remove a foreign object from the human body. Typically, the user manipulates the device 10 at the proximal end 16, which is typically outside of the human anatomy. By manipulating the shaft 12, the motion is translated to the distal end 14 of the device 10, which in turn causes the loop elements 18 to move within the human anatomy. This motion allows the loop elements 18 to catch on the foreign object to be removed from the body. Consequently, the shaft 12 can be designed to have sufficient stiffness, flexibility, pushability and torqueability to accomplish the functions described herein. In some embodiments, a single wire shaft can provide sufficient stiffness, flexibility, pushability and torqueability. In other embodiments, a multiple wire shaft can provide sufficient stiffness, flexibility, pushability and torqueability.

In some embodiments, a hypo tube 20 attaches the loop elements 18 to the shaft 12. The hypo tube 20 has an inner diameter and an outer diameter, and is typically sized such that the shaft 12 and all of the loop elements 18 can fit within the inner diameter of the hypo tube 20. The inner diameter is sized such that there is adequate interference between the hypo tube 20 and the shaft 12 and the loop elements 18, so that the hypo tube 20 can be swaged or crimped circumferentially, mechanically locking the loop elements 18 and shaft 12 together. Additionally, the hypo tube can be radially shaped into a non-circular shape, such as but not limited to a hexagon or square or other rectilinear shape, to further facilitate mechanical fit and locking of said shaft 12 and loop elements 18. In some embodiments, the length of the hypo tube 20 is about at least two times its outer diameter, but can be as short as one times its outer diameter, or as long as twenty times its outer diameter. The loop elements 18 can also be attached to the shaft 12 via welding, soldering, capturing within a coil, or potting within a polymeric or rigid adhesive form, for example.

In some embodiments, the loop elements 18 have a geometric shape which allows them to deploy in a staged manner, where the shape and effective diameter of the snare 10 is dependent upon how far the snare 10 is deployed out of the sheath 22. In a first deployment stage as shown in FIG. 1D, the loops 18 are initially deployed from the sheath 22 and expand, each with a semi-circular shape, a semi-oval shape, or semi-oblong shape, for example, and the effective diameter of the snare 10 is smaller than the effective diameter when the snare 10 is fully deployed. In some embodiments such as a four loop elements 18 embodiment, the snare geometry in the first deployment stage resembles a cloverleaf shape. In some embodiments, as illustrated in FIG. 1E, the cloverleaf shaped loops 18 extend substantially transversely from the shaft 12 and sheath 22. In a second deployment stage as shown in FIG. 1F, the loops 18 extend further from the sheath 22. In some embodiments, in the second deployment stage the loops 18 extend both transversely and axially from the distal end 24 of the sheath 22, thereby providing the snare 10 with extended axial reach in this configuration. In a third deployment stage as illustrated in FIG. 1A, the loops 18 fully expand, reaching the full effective diameter of the snare 10. The snare 10 geometry in the third deployment stage can resemble a substantially complete circle, when viewed along the longitudinal axis of the snare 10 to yield an end view as shown in FIG. 1A, with spoke elements that lead from the circle towards the central hypo tube attachment point. The circle geometry created by the radial edge portions of the loop elements 18 eliminates or reduces gaps between the loop elements 18, which can make it easier for the operator to engage a retrieval element on a foreign object with the snare 10, especially when the retrieval element is located near or around the periphery of the lumen.

To facilitate engagement of the loop elements 18 with the retrieval element, the loop elements 18, when fully deployed, can be sized to conform approximately to the inner diameter of the lumen in which the foreign object is located. This allows full or substantially full apposition between the loop elements 18 and the full circumference of the lumen wall, which enhances the ability of the snare 10 to capture the retrieving element. In some embodiments, the geometry of the fully deployed loop elements 18 can be substantially elliptical, oval or oblong in order to conform to a lumen with a substantially elliptical, oval or oblong cross-sectional geometry. In these embodiments, the major axis of the elliptical or oblong geometry can be sized to conform approximately to the inner diameter of the lumen in which the foreign object is located. In general terms, the geometry of the fully deployed loop elements 18 can substantially match the geometry of the lumen.

Figure 1I:
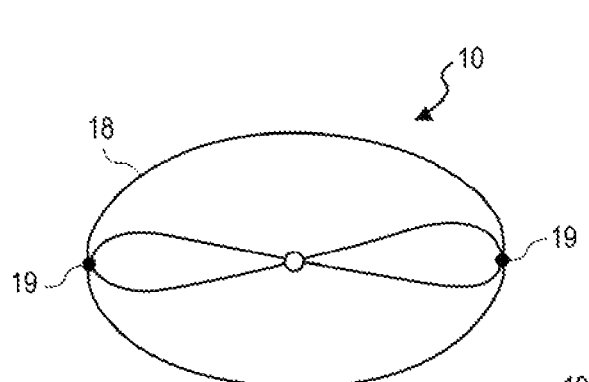
FIGS. 1I-1J illustrate snare embodiments having two loop elements with a substantially elliptical or oblong fully deployed configuration.
Figure 1J:
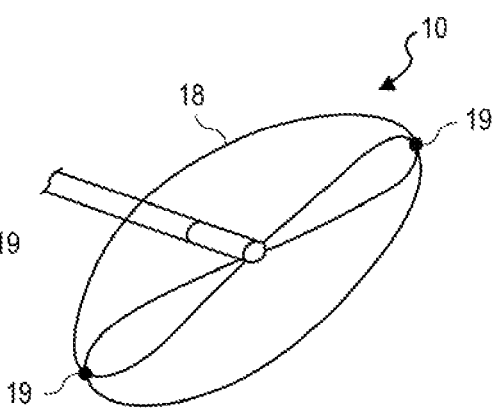
Figure 1K:
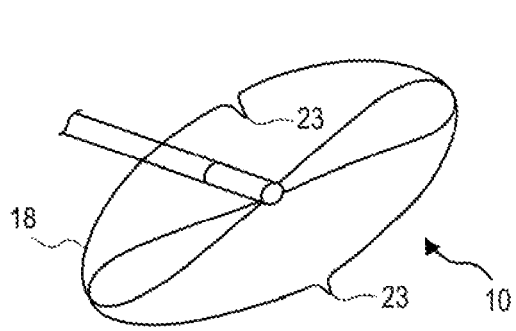
FIGS. 1K-1M illustrate snare embodiments having two loop elements with a substantially elliptical or oblong fully deployed configuration and a loop collapse facilitator.
Figure 1L:
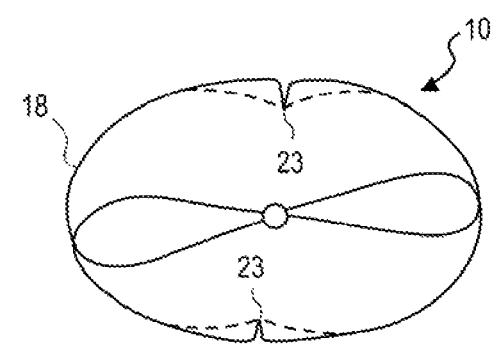
Figure 1M:
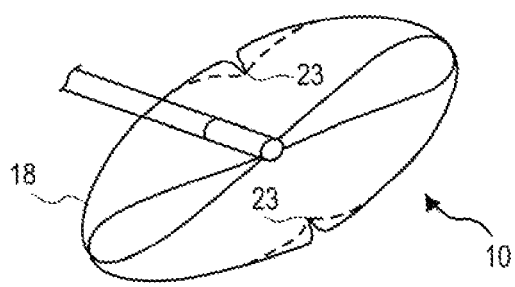
Figure 1N:
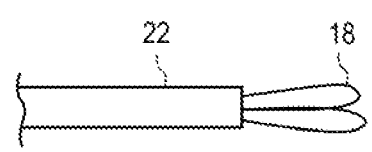
FIGS. 1N-1Q illustrate the stages of deployment of an embodiment of a snare with two loop elements.
Figure 1O:
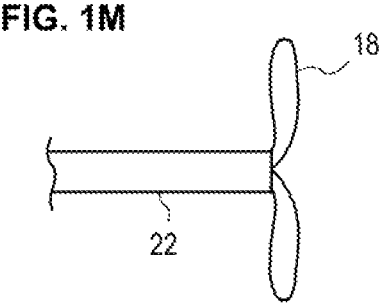
Figure 1P:
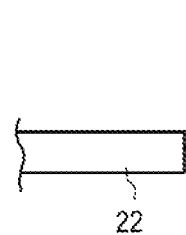
Figure 1Q:
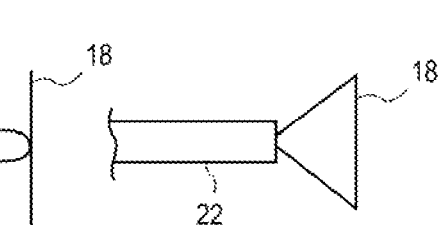

For example, the vena cava may have a generally elliptical or oblong cross-sectional geometry. For use in the vena cava, a snare 10 with loop elements 18 having a substantially elliptical or oblong fully deployed configuration can be used advantageously, as shown in FIGS. 1I-1M, which illustrate snare 10 embodiments having two loop elements 18. In other embodiments, more than two loop elements 18, such as 3, 4 or more loop elements, can be used. By matching the geometry of the deployed loop elements 18 with the geometry of the lumen, full circumferential apposition with the lumen wall can be more readily achieved. In addition, an elliptical or oblong snare 10, which can have a major axis and a minor axis, can be used in lumens having a wide range of sizes because the major axis of the snare can be rotated to provide greater wall to wall reach when needed. Additionally, the loop elements 18 can exhibit both distal and proximal reach, by forming the shape of said loops with a proximally biased curve 58, as shown in FIG. 1S. In some embodiments, the distal reach, D3, is up to about 10 mm, and the proximal reach, D4, is up to about 10 mm, where distal reach and proximal reach are in reference to the distal end of the shaft 12. In other embodiments, D3 and D4 can be greater than or less than the values recited above.

Figure 1R:
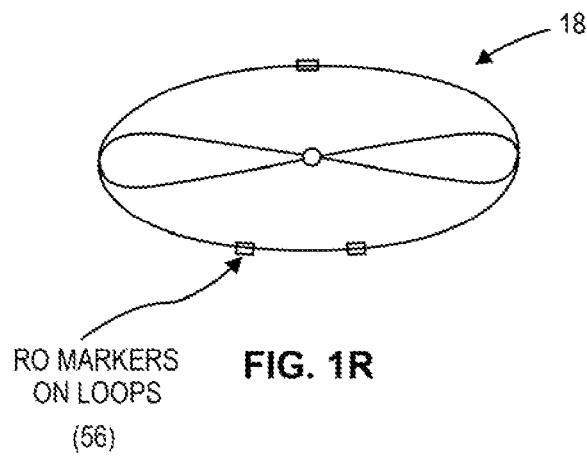
FIG. 1R illustrates a snare embodiment having two loop elements with a substantially elliptical or oblong fully deployed configuration, and a plurality of radiopaque markers disposed on each loop in different patterns, to differentiate each loop element fluoroscopically.
Figure 1S:
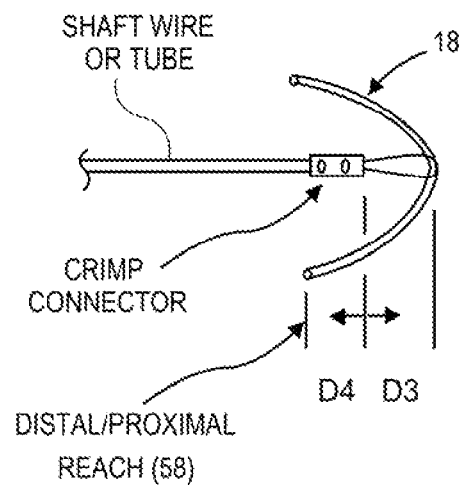
FIG. 1S is a side view of a snare embodiment having two loop elements with a substantially elliptical or oblong fully deployed configuration, showing the loop elements having both a distal and proximal reach.
Figure 1T:
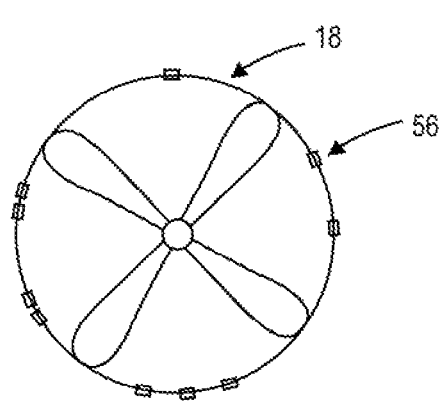
FIG. 1T illustrates a snare embodiment having four loop elements in a substantially circular fully deployed configuration, and a plurality of radiopaque markers disposed on each loop in different patterns, to differentiate each loop element fluoroscopically.

In some embodiments, each individual loop element 18 can employ a single or plurality of radiopaque markers 56, such that each loop element 18 has a different quantity of radiopaque markers 56, or a different pattern of radiopaque markers 56, to allow the operator to visually differentiate and identify each loop element 18 fluoroscopically, as shown in FIGS. 1R and 1T. For example, as illustrated in FIG. 1R, one loop element 18 has a single radiopaque marker 56 while the other loop element 18 has two radiopaque markers 56. Similarly, in FIG. 1T, the first loop element 18 has one radiopaque marker 56; the second loop element 18 has two radiopaque markers 56; the third loop element 18 has three radiopaque markers 56; and the fourth loop element 18 has four radiopaque markers 56.

In some embodiments, the loop elements 18 can be attached or connected together using a variety of techniques, as illustrated in FIGS. 1I and 1J. For example, the loop elements 18 can be connected together by loop connectors 19 which can be made from a piece of wire, metal, plastic or polymer that can be wrapped, twisted, crimped, molded or formed around the two loop elements 18 at, for example, crossover junctions between the loop elements 18. Other techniques for connecting the loop elements 18 together can be used, such as welding or applying adhesives. Alternatively, as shown in FIGS. 1V-1X, the loop elements 18 can be connected together by loop connectors 19b which can be sleeves that are wrapped around or otherwise disposed around the adjacent spoke portions 30 of the loop elements 18. The sleeves can be made of a variety of materials, such as heat shrinkable flexible plastic tubing through which the spokes can be disposed and then secured together by shrinking the tubing around the spokes. For example, the sleeves can be made of PTFE or another biocompatible polymer. The sleeves can provide additional structural stability to the loop elements 18 and allow the loop elements 18 to be advanced or retracted in unison. Without the sleeves, the loop elements 18 may become separated, with for example one loop element facing substantially proximally and the other loop facing substantially distally, which makes control of the snare more difficult and also makes visualization of the snare and object to be retrieved more difficult. Therefore, addition of flexible sleeves, can improve control and visualization of the loop elements during the retrieval process, while still permitting the loop elements to flex and bend and be deployed and manipulated by the user. Additionally, the spoke portions 30 can be twisted together to attach the loop elements 18 together, as shown in FIG. 10A. For example, the spoke portions 30 of adjacent loop elements 18 can be twisted together. Attaching or connecting the loop elements 18 together can reduce the likelihood of unwanted or unintentional loop eversion or loop displacement that can occur during loop deployment, loop manipulation within the lumen and loop retraction.

In some embodiments, the loop elements 18 can include a single or plurality of loop collapse facilitator 23 features, as shown in FIGS. 1K-1M, that facilitates collapse of the loop elements 18 when the loop elements 18, are retracted back into the sheath 22 or when the sheath 22 is advanced over the loop elements 18. The loop collapse facilitator 23 can be a preformed crimp or fold in the loop element 18 that serves as a collapse or folding point for the loop element 18 and therefore initiates or facilitates collapse of the loop element 18 when compressive forces are applied to the loop element 18. In some embodiments, each loop element 18 can have at least one loop collapse facilitator 23.

Figure 1U:
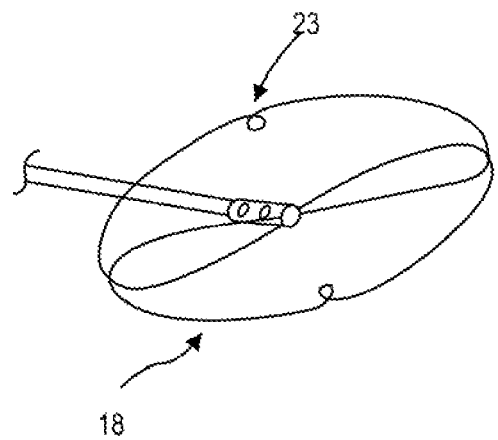
FIG. 1U illustrates another snare embodiment having two loop elements with a substantially elliptical or oblong fully deployed configuration and a loop collapse facilitator.

In addition, the loop collapse facilitator 23 can be oriented in a variety ways. For example, the loop collapse facilitators 23 can be pointed or extend either in a distal direction, as shown in FIG. 1K or a proximal direction (not shown), such that the circumference of the loop elements 18 in the deployed configuration when viewed axially remains in the same shape, such as elliptical, oval or oblong, as compared to embodiments without the loop collapse facilitators 23, as shown in FIG. 1I. In other embodiments, the loop collapse facilitators 23 can be pointed or extend radially inwards as shown in FIGS. 1L and 1M, such that the circumference of the loop elements 18 in the deployed configuration when viewed axially remains in substantially the same shape, such as elliptical, oval or oblong, as compared to embodiments without the loop collapse facilitators 23, as shown in FIG. 1L. In other embodiments, the loop collapse facilitators 23 can be pointed or extend radially inwards as shown in the dotted lines in FIGS. 1L and 1M, such that the circumference of the loop elements 18 in the deployed configuration when viewed axially still remains substantially the same shape, such as elliptical, oval or oblong, but also includes a radially inward indentation, which can be arcuate and taper to a point that extends radially inwards. The size of the indentation can be controlled by the size of the loop collapse facilitator 23 as well as the shape of the taper, as illustrated by the dotted lines and solid lines representing the loop collapse facilitator in FIGS. 1L and 1M. In some embodiments, the loop collapse facilitator 23 can be oriented both distally or proximally as well as radially. In some embodiments, the loop collapse facilitator 23 can employ a loop geometry which provides a hinge point to allow the loop element 18 to fold down and collapse with low force, as shown in FIG. 1U.

FIGS. 1N-1Q illustrate the stages of deployment of an embodiment of a snare 10 with two loop elements 18. As shown in FIG. 1N, during the initial or first deployment stage, the loop elements 18 extend axially out of the sheath 22, thereby providing axial reach to the snare 10 in this configuration, which is suitable as described herein for guide wire retrieval or pacemaker lead retrieval, for example. More generally, this configuration is particularly suitable to retrieve an elongate object that is oriented transversely to the snare axis. In a second deployment stage, the loop elements 18 change from an axial orientation to a transverse or radial orientation, as shown in FIG. 1O, in which the snare 10 has little or minimal axial reach. This configuration may be suitable when the space between the retrieval feature or object and another structure is small and more can more easily be accessed by loop elements with little or minimal axial reach. In the third or full deployment stage, as illustrated in FIGS. 1P and 1Q, the loop elements 18 are fully deployed, forming a circumference that is shaped to conform to the shape of the lumen, such as circular, elliptical, oval, oblong, or any other suitable shape, as illustrated in FIGS. 1I-1M. In the third deployment stage, the snare 10 can have some axial reach and full radial reach which can be configured to provide full circumferential apposition with the lumen wall. The axial reach in the third deployment stage can be increased or decreased to enhance capture of the foreign object, such as a filter, as described herein.

The diameters of the wires can be 0.002"-0.007" each. The wires can be tightly wound together, and then formed into a loop element 18 of the desired shape. The loop element 18 outer radiused edge portion 26 can be angled such that the span of the radiused edge portion 26 is at angle of between about 45 degrees and 90 degrees, relative to the axis of the shaft 12.

The loop element 18 of one embodiment, as illustrated in FIGS. 2A and 2B is made of at least two wires, which are tightly gathered in a twisted configuration, where at least one of the wires is a shape memory nickel titanium wire, and at least one of the wires is of a radiopaque platinum wire. In some embodiments, the twisted configuration can be advantageous over the braided configuration, when a specific stiffness property of the loop elements 18 is desired, by varying the number of wires and wire diameter used in the strand. In some embodiments, the loop element 18 includes 2 shape memory nickel titanium wires and two radiopaque platinum wires. Other materials can be used in place of the nickel titanium and/or radiopaque platinum wires. For example, the nickel titanium alloy, such as Nitinol, can be replaced with a stainless steel wire or polymeric wire. In addition, the radiopaque wire can be replaced with another radiopaque material, such as a platinum-iridium wire, a palladium wire, a gold wire, a tantalum wire, a tantalum-tungsten wire, and the like. In addition, these radiopaque materials can be incorporated into polymeric materials directly or a modified form, such as a salt for example. The radiopaque materials can be bonded or attached to the non-opaque wire in a variety of ways, including wrapping or braiding the radiopaque wire with the non-radiopaque wire together, or by attaching marker bands to the non-radiopaque wire, or by cladding the non-radiopaque wire with the radiopaque material, for example. In many embodiments, the use of various radiopaque markers can be used to indicate the relative location and orientation of the deployed snare 10 in the target area.

FIGS. 3A and 3B depict a view of one embodiment, where just one loop element 18 is shown attached to the shaft 12 for the sake of clarity. The embodiment shown in FIGS. 3A and 3B can have a plurality of loop elements 18, such as two, three, or four loop elements 18, or more than four loop elements 18 as described herein. A snare 10 with more loop elements 18 will have more spoke portions 30 that can engage with the foreign object, which may aid in retrieval of the foreign object. However, an increased number of loop elements 18 may obscure real-time imaging of the snare elements and foreign object, making it more difficult for the operator to correctly identify all the loop elements 18 on the screen, which may interfere with efficient manipulation of the snare 10. In addition, a snare 10 with too many loop elements 18 can end up having a larger compressed diameter due to the many loop elements 18 that are attached to the shaft 12 via, for example, a hypo tube 20 swage connection, as discussed below. As more loop elements 18 are swaged to the hypo tube 20, the diameter of the hypo tube 20 increases in order to accommodate the additional loop elements 20. Increasing the compressed diameter of the snare 10 is generally undesirable for many minimally invasive techniques with which the snare 10 can be used because a larger device requires a larger percutaneous incision, which increases the pain and recovery time for the patient.

In contrast, in some embodiments a snare 10 with fewer loop elements 18, such as two loop elements 18, can be more easily visualized using real time imaging techniques, thereby allowing the operator to accurately identify each loop element 18 and therefore efficiently manipulate the position and orientation of the snare with respect to the foreign object. The two loop element embodiment, as discussed above, can still be capable of achieving complete or substantial circumferential apposition with the lumen wall. In some embodiments with too few loop elements 18, such as a single loop element, the single loop element can be too floppy, and a floppy loop element 18 can be difficult to precisely manipulate and position, making grasping a small retrieval element on a foreign object more difficult.

FIGS. 3A and 3B illustrate the shape of the loop element 18 from two angles; a transverse side view in FIG. 3A and a front axial view in FIG. 3B. The shaft 12 can be attached to the hypo tube 20 via swaging. The hypo tube 20 can also be swaged to the loop element 18. The loop element 18 can be made from a strand of four wires, two Nitinol wires and two platinum wires.

FIG. 4 is an axial view of an embodiment of a loop element 18 and a hypo tube 20. The shape of the loop element 18 includes a radiused edge portion 26 which shares its radial center with the center axis of the hypo tube 20. The radiused edge portion 26 is bounded at each end by a radiused corner feature 28, which transitions the radiused edge portion 26 into two straight spoke portions 30. These straight spoke portions 30 are typically the radius length from the central axis of the hypo tube 20 to the radiused edge portion 26 of the loop element 18. In some embodiments, the straight spoke portions 30 are set at an angle α of approximately 90 degrees, and radiate from the central axis of the hypo tube 20 to the outer radius of the radiused edge portion 26 of the loop element 18.

The loop elements 18 have a geometry that enables them to catch easily on foreign objects in the human anatomy. In some embodiments as shown in FIG. 4, the loop element 18 has a "D" shape which resembles a pie slice with rounded corners, when viewed axially along the device axis. This D shape includes a radiused edge portion 26, which shares a radial center with the axis of the shaft of the device. The radiused edge portion 26 is bounded at either end by a radiused corner portion 28 which transitions the radiused edge portion 26 into two straight spoke portions 30. In some embodiments, the radiused corner portion 28 bends about 90 degrees towards the central axis of the shaft 12.

In some embodiments, the two straight spoke portions 30, which radiate from the central axis of the hypo tube to the outer radius of the radiused edge portion 26, are set at an angle α of about 90 degrees, for a snare 10 with four loop elements 18. In some embodiments, the angle α between the two straight spoke portions 30 can be less than 90 degrees when, for example, the snare 10 has more than four loop elements 18, such as an angle of about 60 degrees for a snare 10 with six loop elements 18, or an angle of about 72 degrees for a snare 10 with 5 loop elements. To generalize, in some embodiments, the angle in degrees between the straight spoke portions 30 can be determined by dividing 360 by the number of loop elements 18 in the snare 10. This results in a configuration where the loop elements 18 cover an entire circle of space when viewed along the axial axis. Therefore, in an embodiment of the snare 10 with three loop elements 18, the angle between the two straight spoke 30 portions can be about 120 degrees. In some embodiments, the angle α between the straight spoke portions 30 can be greater than as determined using the formula set forth above, which results in an overlap of portions of the loop elements 18 with adjacent loop elements 18. In some embodiments, the angle between the two straight spoke 30 portions is greater than the value calculated in the formula set forth above, where an angle of about 5 to 15 degrees ensures that there is minimal or no gap about the perimeter of the snare, to form a closed circle.

Figure 12:
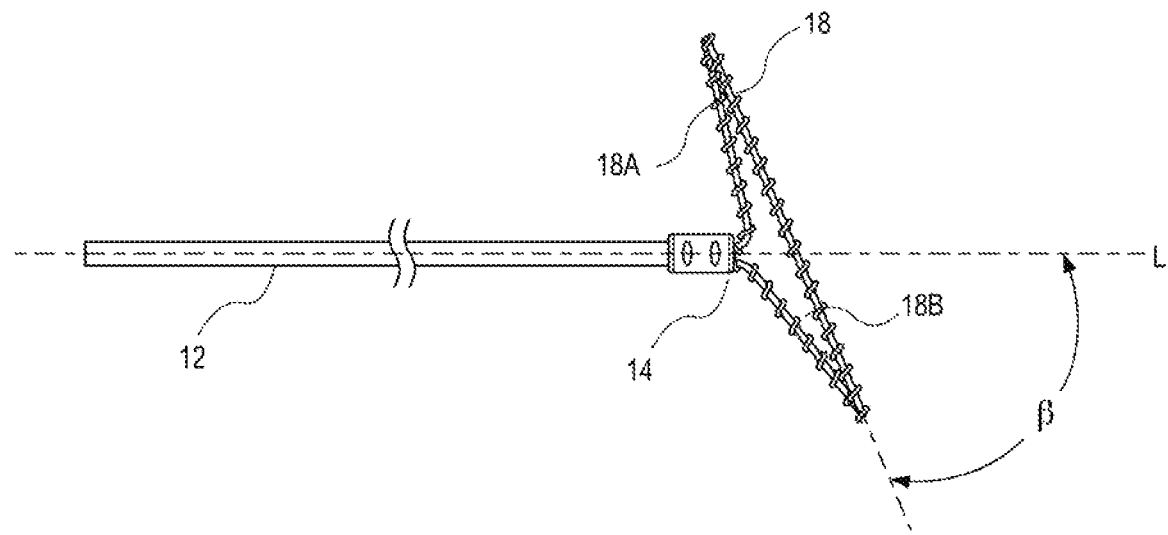
FIG. 12 is a side view of an embodiment of the shaft, hypo tube, and a single loop element for illustrative purposes. The actual snare device can have a plurality of loop elements. The view illustrates an embodiment of the loop element wherein the angle of the radius portion of the loop element is typically about 45 degrees from the central axis of the hypo tube component.
Figure 13:
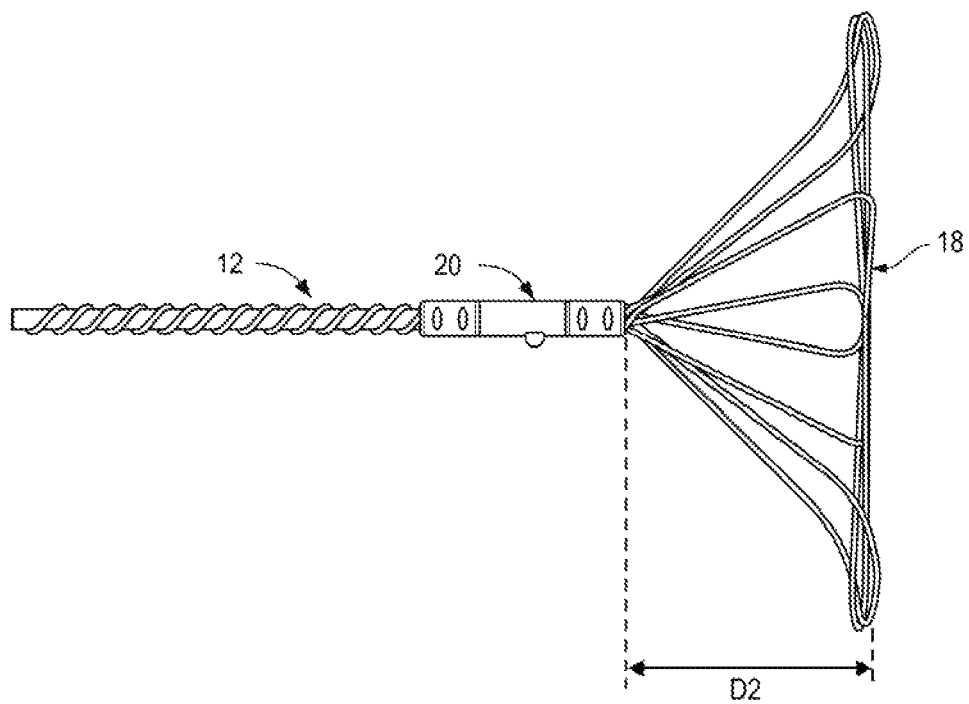
FIG. 13 is a side view of an alternate embodiment of the snare device where the shaft is made from a twisted strand, and the loop elements form a circular shape in a single plane 90 degrees from the axis of the shaft.

In some embodiments, from a transverse view, the large radiused edge portion 26 of the loop element 18 can be angled between about 90 degrees and about 30 degrees relative to the axis of the shaft 12 of the device 10, as shown in FIG. 12. This edge can also be substantially or exactly 90 degrees from the shaft axis, forming a flat, single plane circle when viewed transversely, as shown in FIG. 13.

In other embodiments, from a transverse view, the large radiused edge portion 26 of the loop element 18 can be angled at an angle β that is from about 5 to 45 degrees relative to the longitudinal axis L of the shaft 12 of the device 10, as shown in FIGS. 3A and 12. Such a configuration where the radiused edge portion 26 is angled less than 90 degrees results in a propeller like configuration where the loop element 18 has a pitch and axial reach both proximal and distal the end of the shaft 12 and/or sheath 22. As illustrated in FIG. 12, the loop element 18 has a portion proximal to the distal most portion of the shaft and a portion distal to the distal most portion of the shaft, as shown by the dotted line which divides loop element 18 into the proximal portion 18A and the distal portion 18B. In addition, the propeller configuration can result in the opening of the loop elements 18 being oriented in both a plane transverse to the snare axis and a plane parallel to the snare axis.

In these embodiments, the axial deployment length at full deployment of the loop elements 18 is relatively short when compared to some prior art devices which resemble the intermediate deployment configuration illustrated in FIG. 1F for some embodiments. A long axial deployment length can be beneficial in some situations, such as capturing a guide wire that is oriented generally transversely to the snare 10, or capturing a retrieval element on a foreign object when the retrieval element is located at or near the center of the lumen. A short axial deployment length can be beneficial in other situations, such as capturing a retrieval element that is located at or near the periphery of the lumen. In some embodiments, loop elements 18 with a long axial deployment length can inadvertently capture structural elements on the foreign object, such as frame anchors on a filter, rather than the retrieval element which is specifically designed to be engaged by the snare. When a structural element such as a frame anchor is captured instead of the retrieval element, the filter may not be able to be withdrawn into the sheath 22 and be removed. In addition, the loop elements 18 may get tangled up with the frame anchors and other structural elements more easily when the axial length is long. This can be a problem with some prior art devices, such as the EN Snare® retrieval device, which has a long axial reach. For at least these reasons, a short deployment length can be advantageous over a long deployment length in certain situations. In some embodiments, the axial deployment length of the loop elements 18 can be less than the distance between the retrieval element and the support member or anchor of the filter, thereby reducing the likelihood that the loop elements 18 will inadvertently engage the anchors on the support members. In some embodiments, the axial deployment length of the loop elements 18 can be less than the distance between the retrieval element and the support member crossover or the material capture structure of the filter. In some embodiments, the axial deployment length of the loop elements 18 can be less than the distance between the retrieval element and any structure on the filter in which the loop elements can get entangled with or that interfere with the function of the loop elements 18.

In addition to the axial deployment length, loop elements of prior art devices lack substantially complete circumferential apposition with the vessel wall, which makes it difficult to retrieve objects near the periphery of the blood vessel lumen. In contrast, embodiments of the snare disclosed herein achieve substantially complete circumferential apposition which facilitates retrieval of objections, such as retrieval elements on filters, that are located near the periphery of the blood vessel lumen.

Figures 6A, 6B:
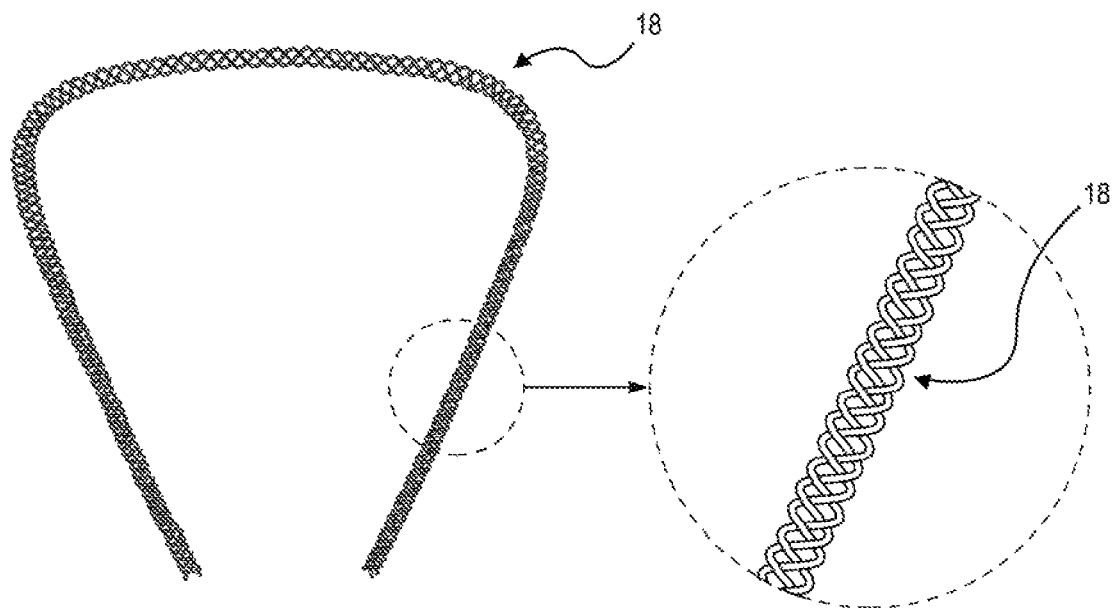
FIG. 6A illustrates an embodiment of a single loop element, using a plurality of wires which are braided together to form a strand.
FIG. 6B illustrates a close up view of a portion of the single loop element strand shown in FIG. 6A.
Figure 7:
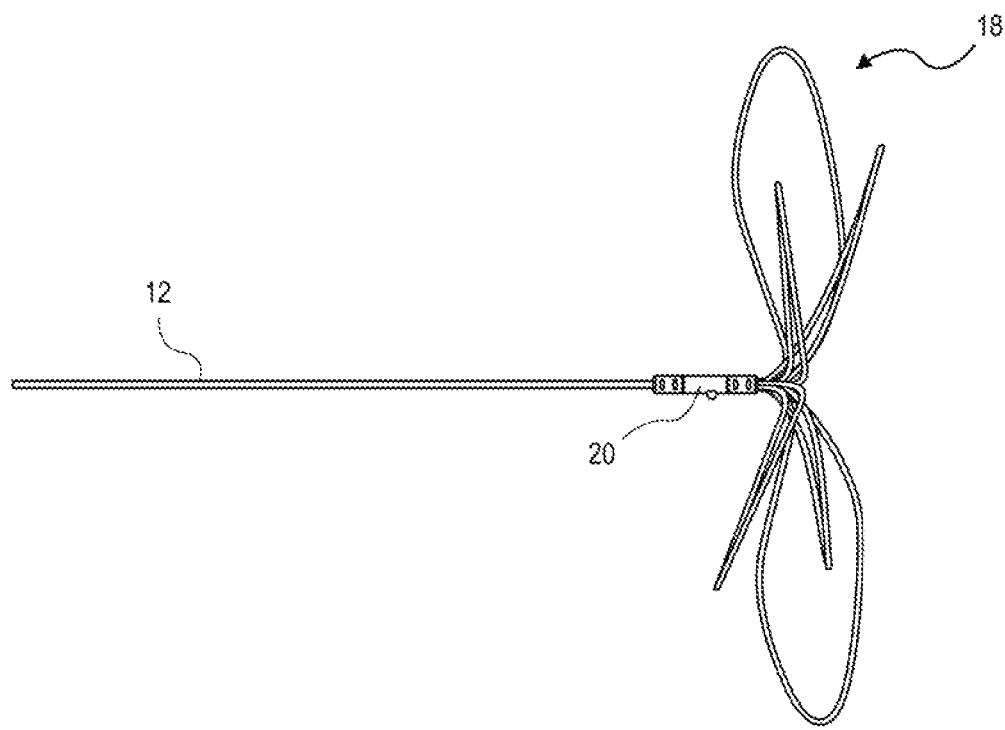
FIG. 7 is a side view of an embodiment of a snare device using single wire loop elements, and a steel hypo tube which attaches the loops to the shaft via a crimp process.
Figure 8:
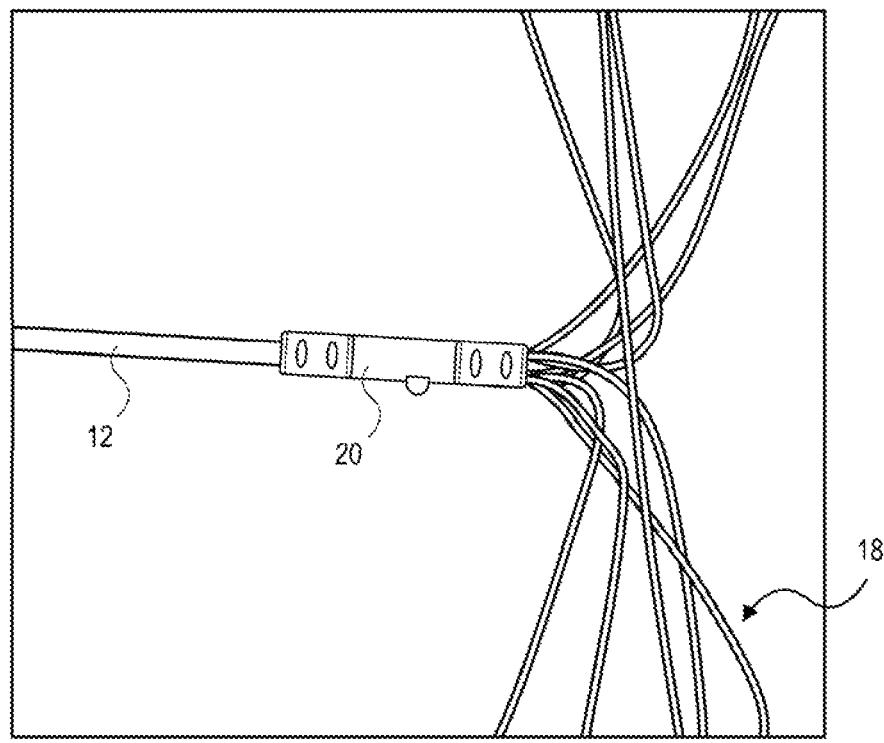
FIG. 8 is a close up view of the snare device shown in FIG. 7, further illustrating the steel hypo tube which attaches the loops to the shaft via a crimp process.
Figure 9:
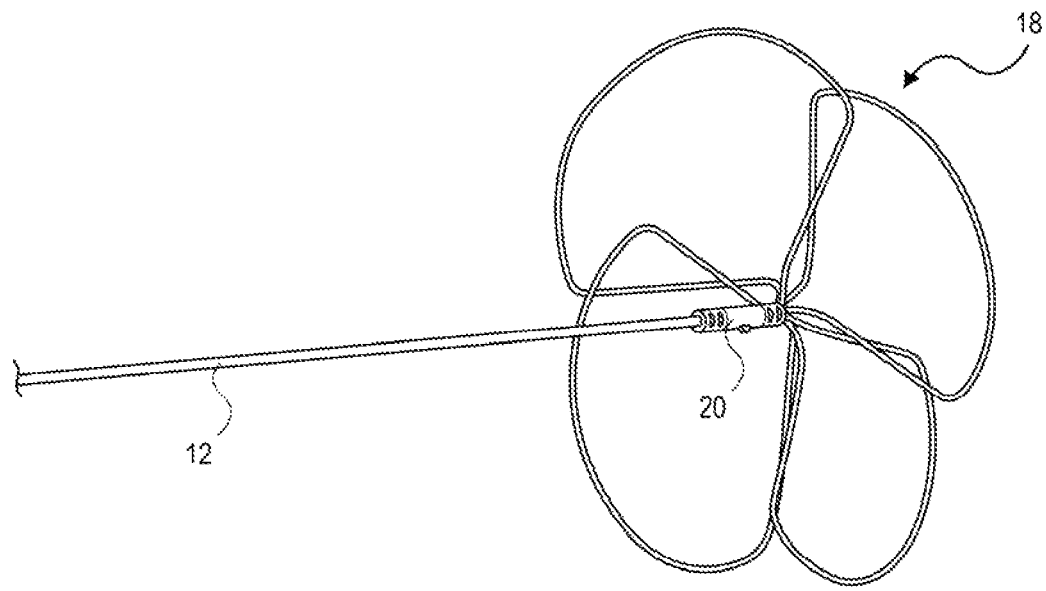
FIG. 9 is a perspective view of the snare device shown in FIG. 7.

FIGS. 5A and 5B illustrates an embodiment of a loop element 18 made of four round wires, which are tightly gathered in a twisted configuration, where two of the wires are of shape memory nickel titanium wire, and two of the wires are of a radiopaque platinum wire. The diameters of the wires can be about 0.004" each. The wires are tightly wound together, and then formed into a loop shape. In some embodiments, the loop outer radius is angled such that the span of the radius is at angle of between about 45 degrees and 90 degrees, relative to the axis of the shaft. FIGS. 6A and 6B illustrates a similar embodiment of a loop element 18 made of four wires, except that the wires are braided together rather than twisted together to form the loop element 18.

Figure 10:
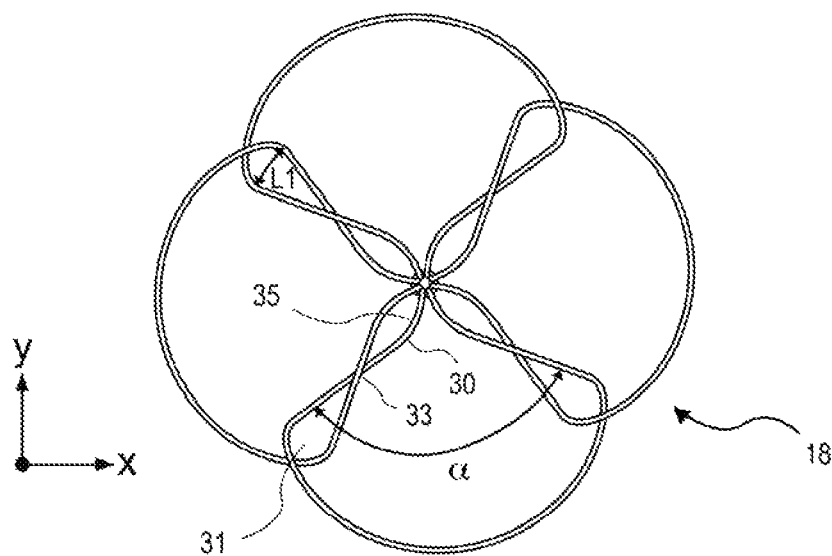
FIG. 10 is an end view of the snare device shown in FIG. 7. The view illustrates how the loops overlap laterally, with the outer perimeter forming a circular shape.
Figure 10A:
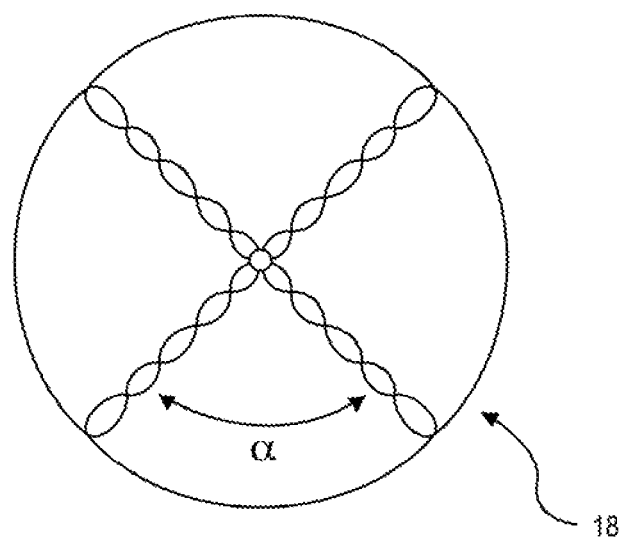
FIG. 10A is an end view of another embodiment of a snare device. The view illustrates how the loop elements are twisted together laterally, with the outer perimeter forming a circular shape.

One alternate embodiment of the device 10, illustrated in FIGS. 7-10, includes a series of loop element structures 18 mounted in a substantially circular geometry when viewed along the longitudinal axis. In some embodiments, the loop elements 18 extend substantially transversely with respect to the longitudinal axis. In some embodiments, the outer circular perimeter defined by the loop elements 18 is substantially continuous and does not have gaps. In some embodiments, the overlap 31 between the loop elements 18 is as described above for FIG. 1A, where the overlap 31 covers a pie shaped region that extends from the outer circumference of the loop elements to the center where the loop elements are attached to the shaft. In other embodiments, the overlap 31 between the loop elements 18 can change as the loop elements 18 are further extended out of the sheath. For example, as shown in FIG. 10, the loop elements 18 can have an overlap 31 that occurs over approximately the middle to distal portion of the loop elements 18. As illustrated in FIG. 10, the overlap 31 begins at crossover points 33 between the spokes 30 of the loop elements 18. In some embodiments, as the loop elements 18 are retracted back into the sheath, the crossover points 33 move closer towards the center, until the crossover points merge into the center, resulting in an overlap configuration similar to that illustrated in FIG. 1A. In addition to the variable overlap regions, the embodiment illustrated in FIG. 10 has interior gap portions 35 between the loop elements. These interior gap portions 35 extend radially inwards from the crossover points 33, and can decrease in size and disappear as the loop elements 18 are retracted back into the sheath. In these embodiments, the loop elements 18 can have a radial span that can be defined by the angle α, and an overlap with a span L1, similar to that described above for FIG. 1A. In these embodiments and in others, the overlap portions can also act as additional snaring portions which increase the likelihood that a portion of the device engages the object to be retrieved.

In some embodiments, the loop elements 18 can be attached to a shaft 12 via a swaged or crimped hypo tube 20. These loop elements 18 can be made of two or more wires, including at least one Nitinol wire and at least one platinum wire. As illustrated in FIGS. 7-10, in some embodiments the most distal part of the device 10 can be the loop elements 18 because the device 10 does not have a distally extending control member that can be found in some prior art devices, such as the grasping device disclosed in U.S. Pat. No. 7,753,918. In some embodiments, the presence of a control member may interfere with retrieval of the foreign object, such as a filter, by getting entangled with the filter, making it advantageous for some embodiments to not have a distally extending control member. In some embodiments, the loop elements 18 can be angled or have a pitch with respect to the longitudinal axis.

Figure 11:
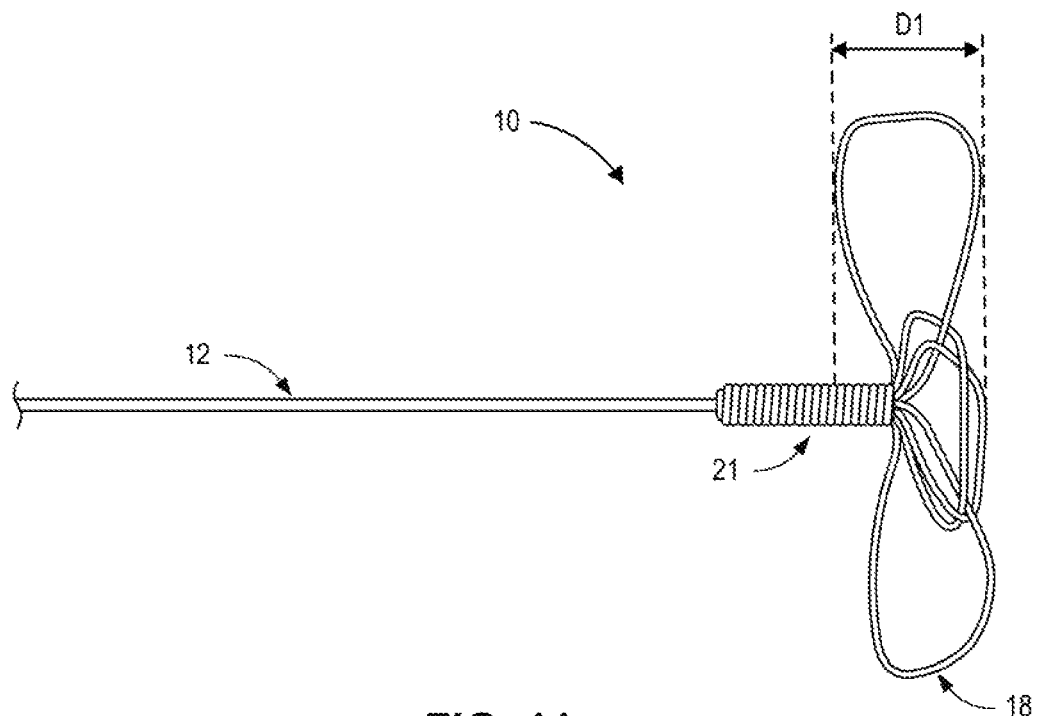
FIG. 11 is a side view of an embodiment of a snare assembly, where the loop elements are attached to the shaft element with a wire coil.

FIG. 11 illustrates another embodiment of the snare 10 where the loop elements 18 are attached to the shaft 12 with a wire coil 21. In some embodiments, the wire coil 21 can be a separate wire that can be wrapped around the proximal portions of the loop elements 18. In other embodiments, the proximal portions of the loop elements 18 can be wrapped around the distal end of the shaft 12 in order to form the wire coil 21. As additionally shown in FIG. 11, the loop elements 18 can extend axially, or in other words, have an axial depth, D1, that can be between about 1 to 10 mm. This axial reach allows loop elements 18 to effect capture of an object, such as a retrieval element of a filter, via rotation about the longitudinal axis of the snare. In some embodiments, the axial depth, D1, is less than the distance between a retrieval element on a filter and the closest anchor to the retrieval element, as further described below.

Figure 14:
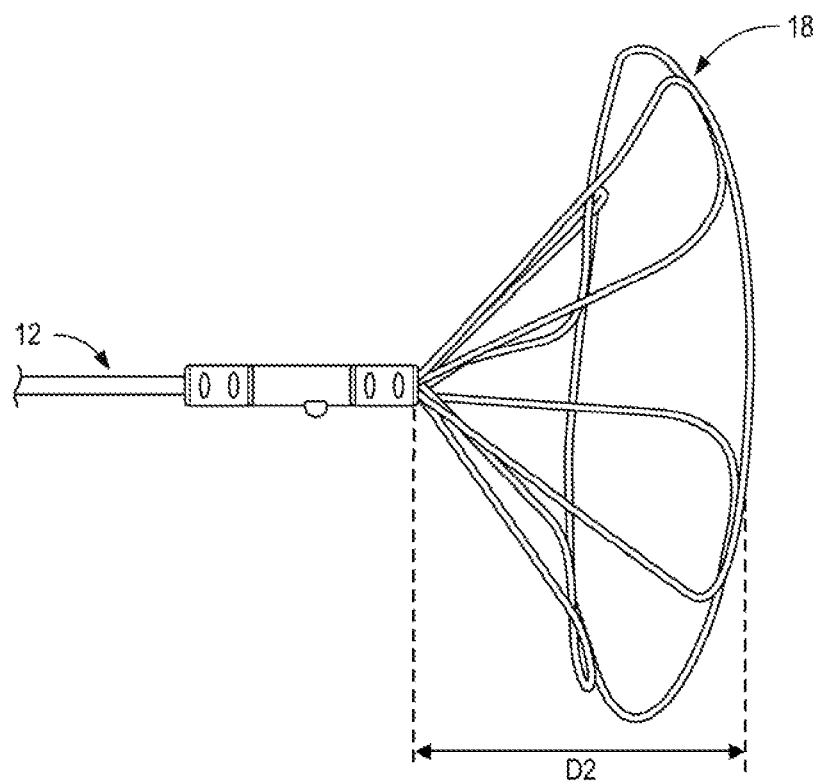
FIG. 14 is a horizontal isometric view of the alternate embodiment shown in FIG. 13, illustrating the flat circular shape of the outer perimeter of the snare loops.
Figure 15:
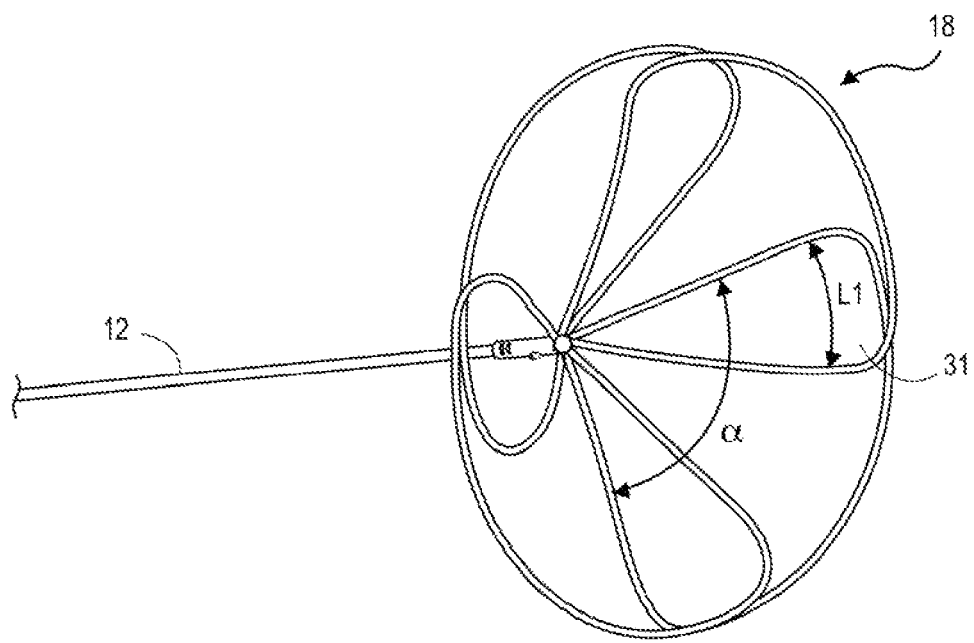
FIG. 15 is a frontal angled view of the alternate embodiment shown in FIG. 13, illustrating the circular shape of the snare outer perimeter, as well as the straight portions of each loop overlapping the adjacent loop to form a closed circle with no gaps about the perimeter.

Another alternate embodiment, as illustrated in FIGS. 13-15, utilizes a twisted strand shaft 12 made of four 0.010" Nitinol wires. This shaft 12 is attached to twisted strand loops elements 18 using a hypo tube 20 using silver solder, for example. After full deployment, the loop elements 18 form a substantially circular geometry which is in a single plane typically 90 degrees from the axis of the shaft 12. In some embodiments, as illustrated, the loop elements 18 extend both transversely and axially with respect to the longitudinal axis of the shaft 12, forming a cone-like structure with a circular base defined by the distal edge portions of the loop elements 18. The axial reach, D2, or extension of the circular portion past the distal end of the shaft can vary and can depend on and be less than, for example, the distance between the retrieval element and a particular filter structure, such as an anchor, support member, support member crossover, or material capture structure of the filter, as further described herein. The axial reach, D2, can be between about 1 to 10 mm. In addition, the loop elements 18 can a region of overlap 31 and can have a radial or circumferential span defined by the angle α, as described above with reference to FIGS. 1A and 4.

In some embodiments, this design offers several key features and capabilities, for example:

1. Loop Design

The design of the loop elements allows for deployment in different size lumens, and can conform to variations in lumen anatomy such as tapering, curvature, and angulations. This conformance feature can also enable the device to achieve full radial apposition with the target lumen regardless of lumen diameter or circularity. The loop configuration allows the device to catch a foreign object no matter where the object is located within the luminal space, since the loops reach full radial apposition within the lumen. The design of the elements allows the snare to fit into a very small guiding sheath, facilitating navigation through tortuous anatomies. The angled design of the loop radius allows the device to have axial reach both distal and proximal to the point where the loops are attached to the shaft, enabling the loops to locate foreign objects with minimal forward and backward axial manipulation of the device by the user. The non-angled design of the loop radius allows the device to have a flat, single plane circle geometry, enabling the loops to locate foreign objects with which may be against the vessel wall or partially embedded in the vessel wall. The loops can be made radiopaque, which allows visualization of the loop under fluoroscopy. Additionally, each individual loop element can employ a single or plurality of radiopaque markers such that each loop element has a different quantity of radiopaque markers, or a different pattern of radiopaque markers, to allow the operator to visually differentiate and identify each loop element fluoroscopically.

2. Shaft Design

The diameter and mechanical properties of the shaft, such as tensile strength, stiffness and/or elasticity, allows the user to manipulate the loops easily, by transferring axial and torsional motion from the proximal end of the device down to the distal end of the device. The diameter of the shaft allows for it to fit within a small diameter guiding sheath. The diameter of the shaft provides tensile support and strength to allow for high forces that may be required for removing a foreign object from the human anatomy. The shaft can be either solid or hollow, allowing the passage of devices, such as a guidewire, through the shaft. The shaft can be of a single element such as a wire, or a construction of a plurality of elements which are braided or stranded together. The shaft can be of a radiopaque material, to facilitate fluoroscopic visualization.

3. Hypo Tube Design

The inner diameter of the hypo tube allows the loop wires and shaft wire to fit snugly within the inner diameter, to facilitate mechanical swaging, soldering, or crimping of said hypo tube, mechanically locking the elements together. The outer diameter of the hypo tube provides adequate wall thickness to allow mechanical swaging or crimping of the hypo tube to provide a strong mechanical attachment, without cracking the hypo tube. The hypo tube can be of a radiopaque material, to facilitate fluoroscopic visualization. Additionally, the hypo tube can be radially shaped into a non-circular shape, such as but not limited to a hexagon or square or rectilinear shape, to further facilitate mechanical fit and locking of the shaft and loop elements.

In some embodiments, the fundamental design elements which achieve these features include, for example: (1) a plurality of loop elements, which are attached to a shaft via a hypo tube; (2) loops which are designed to be flexible and radiopaque; (3) loops which can be collapsed within a guiding catheter, and deployed outside of the guiding catheter; (4) loops which can reach full circular apposition within the luminal space in a human body; (5) loops which are attached to a shaft distally, which extend laterally towards the wall of the vessel of a human body; (6) loops which are angled relative to the axis of the shaft, typically less than 91 degrees and typically greater than 1 degrees; (7) loops which employ an attachment that is typically a crimped or swaged hypo tube; (8) a shaft which is attached to the loops; (9) a shaft having a diameter allows it to fit within a small diameter guiding catheter; (10) a shaft which can be either solid or hollow; (11) a shaft made of a material which can be polymeric, or can be of a metal such as but not limited to nickel titanium; and (12) a shaft having a length designed to enable the user to position the loops at a desired location to remove a foreign object from a human body.

In some embodiments, the snare device 10 is designed for placement into a guiding sheath 22, being advanced through said sheath 22, deploying near a foreign object located within the human anatomy, capturing said object, and removing the object from the human anatomy. The shape of the loop elements 18 allows them to conform to the diameter of the vessel in which they are deployed into, allowing easier capture of the foreign body with less manipulation.

The device 10 enables a user to capture a foreign object located within the human anatomy, grasp said object in a controlled manner, and retrieve and remove said object from the human anatomy. Examples of foreign objects which might be removed from the human anatomy include implants such as stents, guidewires, leads, filters, and valves, and organic objects such as kidney stones or calcified emboli. For example, a snare 10 can be used to capture a vena cava filter and pull it into a retrieval sheath 22 for removal from the patient.

Figure 16:
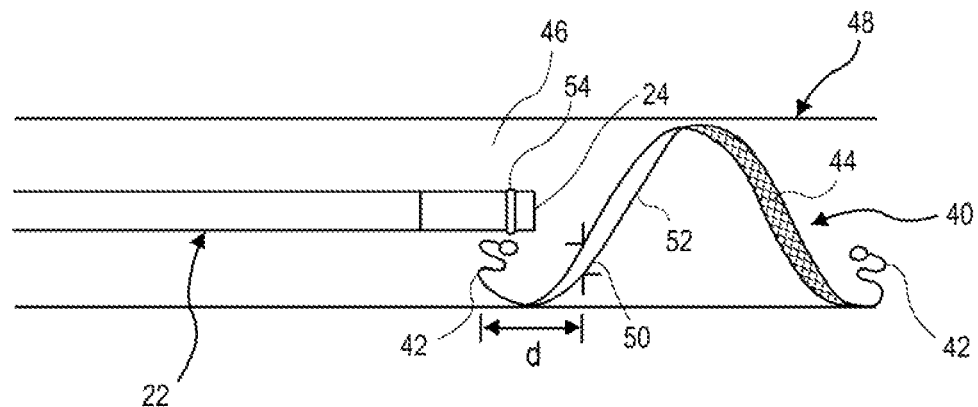
FIGS. 16-19 illustrate embodiments of methods of using any of the snares 10 disclosed herein.

FIGS. 16-19 illustrate embodiments of methods of using any of the snares 10 disclosed herein. As shown in FIG. 16, the snare 10 can be advanced through one or more retrieval sheaths 22 and up to the site of a deployed filter 40, which, for example, can be located within the lumen 46 of a blood vessel 48. In some embodiments, the snare 10 can be pre-loaded into a sheath 22 which can be inserted into the patient via a minimally invasive procedure, such as a percutaneous insertion technique. In some embodiments, the distal end 24 of the sheath 22 can be advanced to or proximally to the retrieval element 42 of the filter 40. In some embodiments, the distal end 24 of the sheath 22 is advanced just past, i.e. just distal, the retrieval element 42, taking care to avoid advancing the distal end 24 into the other elements of the filter 40, such as the filter portion 44 or anchors 50 on the filter frame 52, which would indicate that the distal end 24 had been advanced too far. In some embodiments, the distal end 24 is advanced to a location distal the retrieval element 42 and proximal the anchors 50 closest the retrieval element 42. In some embodiments, the sheath 22 includes a radiopaque marker 54 located near the distal end 24 of the sheath 22 that facilitates alignment of the distal end 24 with respect to the filter 40. For example, the operator can align the radiopaque marker on the sheath 22 with the radiopaque retrieval element 42 of the filter 40 under fluoroscopy, which results in the distal end 24 of the sheath being correctly positioned for loop element 18 deployment, which in some embodiments as described herein is located between the retrieval element 42 and the anchor 50 closest to the retrieval element.

Figure 17:
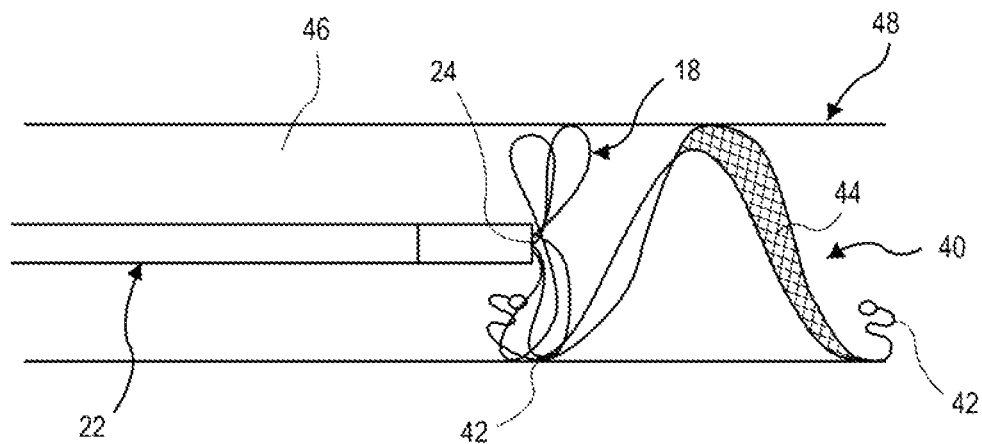

As illustrated in FIG. 17, the snare 10 is then deployed into the vessel 48. As described above, deployment of the snare 10 can include three deployment phases. In some embodiments, deployment of the snare 10 can include less than three deployment phases, such as one or two deployment phases, while in other embodiments, deployment of the snare 10 can include more than three deployment phases. FIG. 17 illustrates full deployment of the snare 10 into the vessel 48 with the loop elements 18 in a propeller-like configuration that provides some axial reach both proximal and distal to the distal end 24 of the sheath 22. In some embodiments, the axial reach in the distal direction can be less than the distance d between the retrieval element 42 and anchor 50, thereby reducing the likelihood that the loop elements 18 become entangled with or caught on the anchor elements 50 of the filter during loop element 18 deployment and manipulation. In some embodiments, the distance d can be between about 5 to 20 mm The region between the retrieval element 42 and the anchor 50 forms a zone of action in which the loop elements 18 can be deployed and manipulated to effect capture of the retrieval element 42. In some embodiments, the loop elements 18 can have a pitch like the blades of a propeller such that the openings of the loop elements 18 are oriented in both a plane transverse to the snare 10 axis and a plane parallel to the snare axis. This allows the loop elements 18 to capture the retrieval element 42 either by moving the loop elements 18 axially in a proximal or distal direction or by rotating the loop elements 18 about the snare axis. In some embodiments, the loop elements 18 are deployed distal the retrieval element 42 and proximal the support member of the filter, such that the loop elements 18 achieve substantial apposition with the full circumference of the lumen wall, which is advantageous for capturing retrieval elements located near the periphery of the lumen. The deployed loop elements 18 can be withdrawn or retracted proximally to engage the retrieval element.

Figure 18:
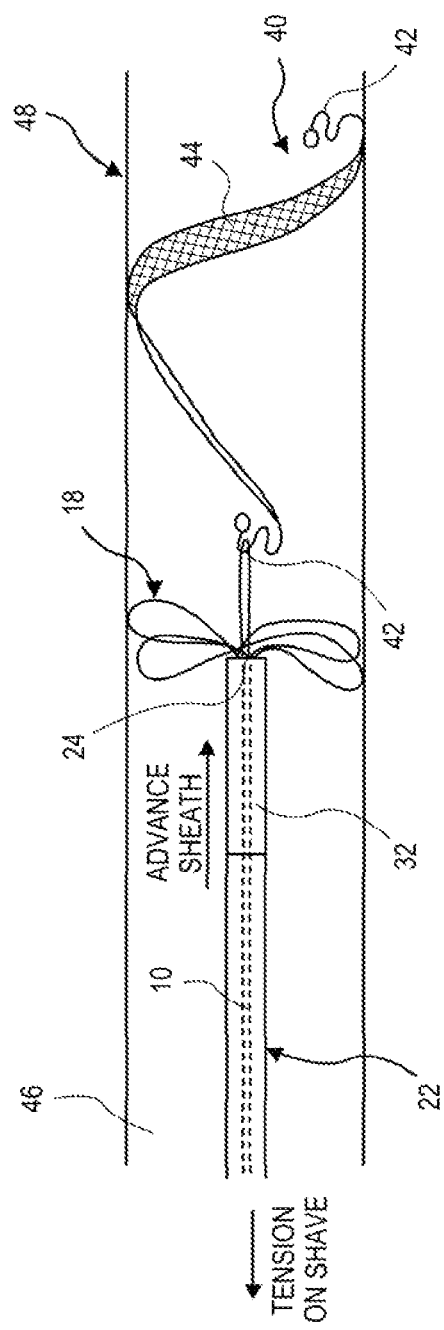
Figure 19:
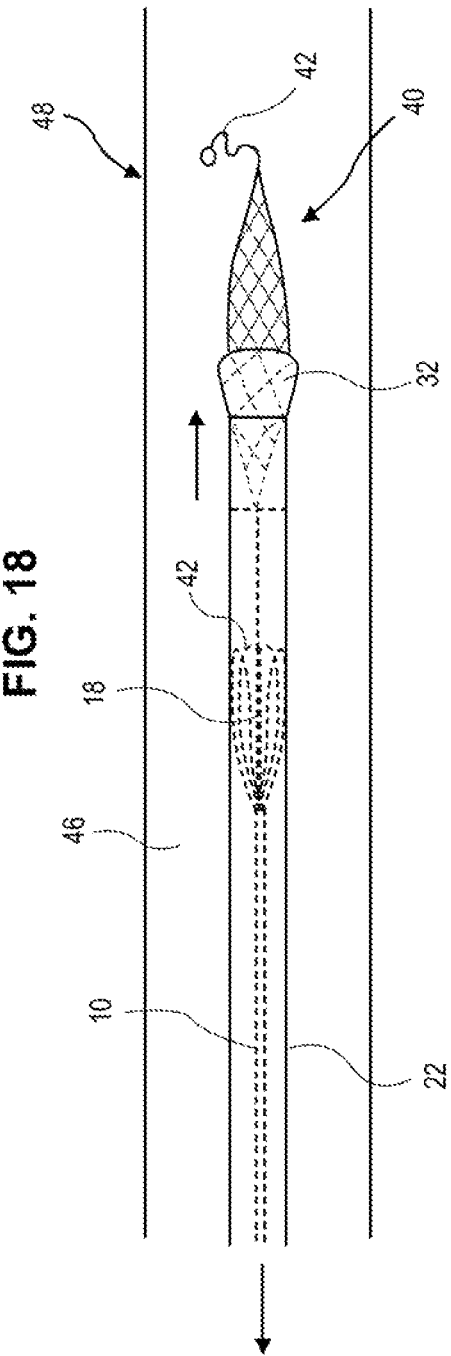

FIGS. 18-19 illustrate the loop element 18 engaged with the retrieval element 42 of the filter 40 and the subsequent collapse of the filter 40 into the sheath 22. After the retrieval element 42 is secured, the snare 10 is held under tension while the sheath 22 is advanced over the filter 40, thereby collapsing the filter 40 into the ID of the sheath 22. In some embodiments using both an inner sheath 22 and an outer sheath, the retrieval element 42, and optionally a portion of the filter 40, is first retracted or pulled into an inner sheath 22, in order to secure the filter 40 to the snare 10 and to prevent or reduce unfurling of the tail portion of the filter 40, before the outer sheath is advanced over the rest of the filter 40.

As the sheath 22 is advanced over the filter 40, the flexible distal tip portion 32 of the sheath 22 can expand and invert over the filter 40, providing a ramp in which the filter 40 can be drawn into the sheath 22. In some embodiments, the inversion of the distal tip portion 32 can be initiated by contact with specific structures on the filter, such as the retrieval element and/or anchors on the filter frame. In some embodiments, the snare 10 can be retracted in the proximal direction while the sheath 22 is advanced in the distal direction to capture the filter 40 within the sheath 22. In other embodiments, the snare 10 can be retracted in the proximal direction while the sheath 22 is held relatively immobile, i.e. neither advanced nor retracted, to capture the filter 40 within the sheath 22. In some embodiments, the entire filter 40 can be retracted into or captured by the inner sheath.

Another example is the use of a snare 10 to grasp and extract loose kidney stones from a patient's kidneys. The snare 10 is advanced through one or more sheaths 22, up to the site of the loose kidney stone. The snare 10 is then deployed and engaged with the stone. Next, the snare 10 is pulled into the sheath 22, or the sheath 22 advanced over the snare 10, drawing the stone into the distal ID of said sheath 22.

As described above, the retrieval system can include a plurality of different components, such as a guide wire, a snare 10, an inner sheath and an outer sheath 22. The proximal ends of these components are generally located outside the patient's body so that the operator can manipulate each of the components by grasping the proximal portion of the components and moving the component in a proximal or distal direction. Often, the proximal portions or ends of the components are or can be reversibly secured or fixed to one another in a proximal handle portion, using a rotatable or twist fitting, such as a luer lock, for example. Because one hand of the operator is often used to manipulate the component, only one hand is free to disconnect or connect the fittings, which can be difficult to do for a rotatable luer lock fitting. In addition, the twisting or rotation of the twist fitting can lead to unintentional and undesired twisting or rotation of the snare device.

Figure 20:
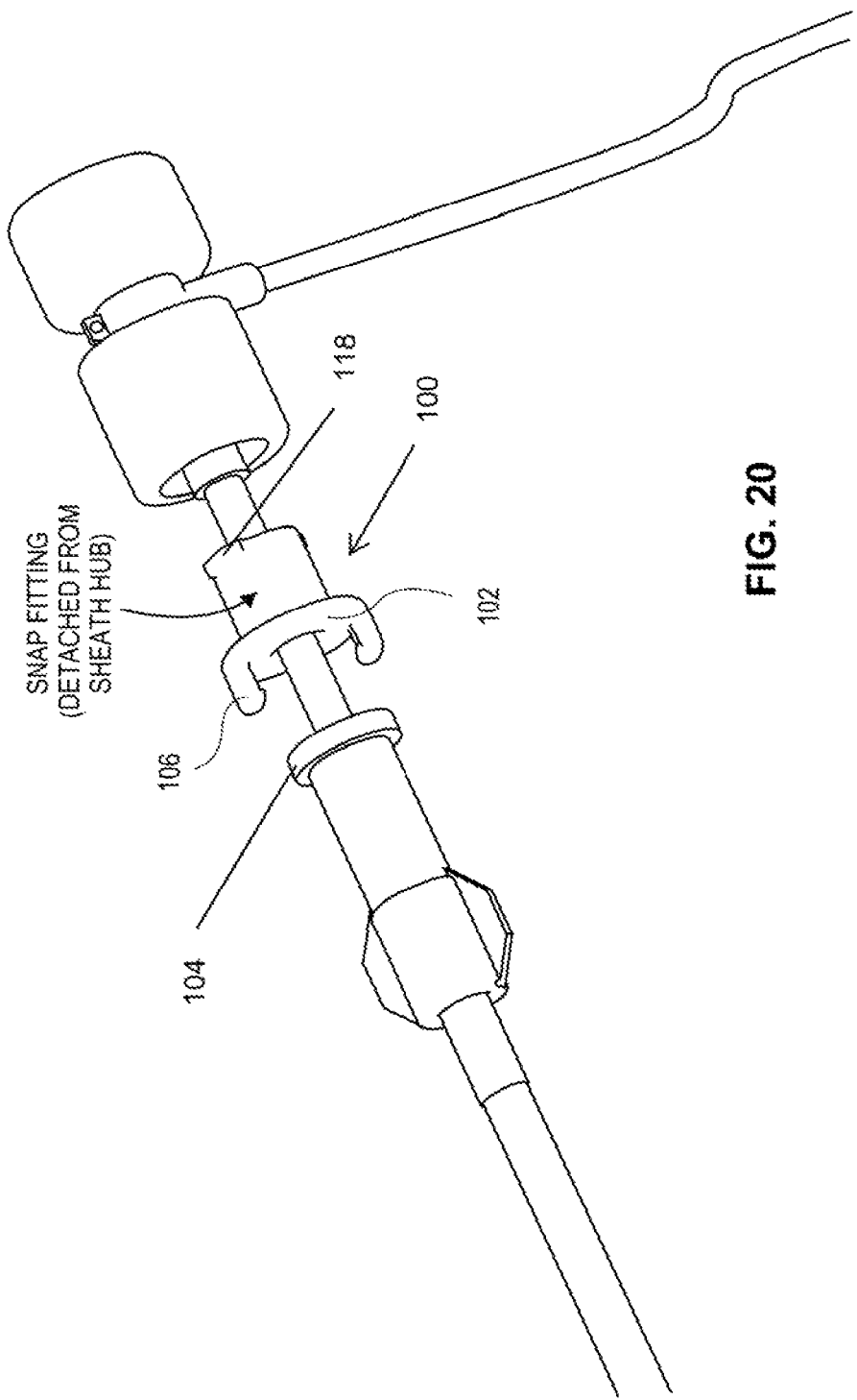
FIGS. 20-22 illustrate embodiments of a snap fitting that can be used with the snare.
Figure 21:
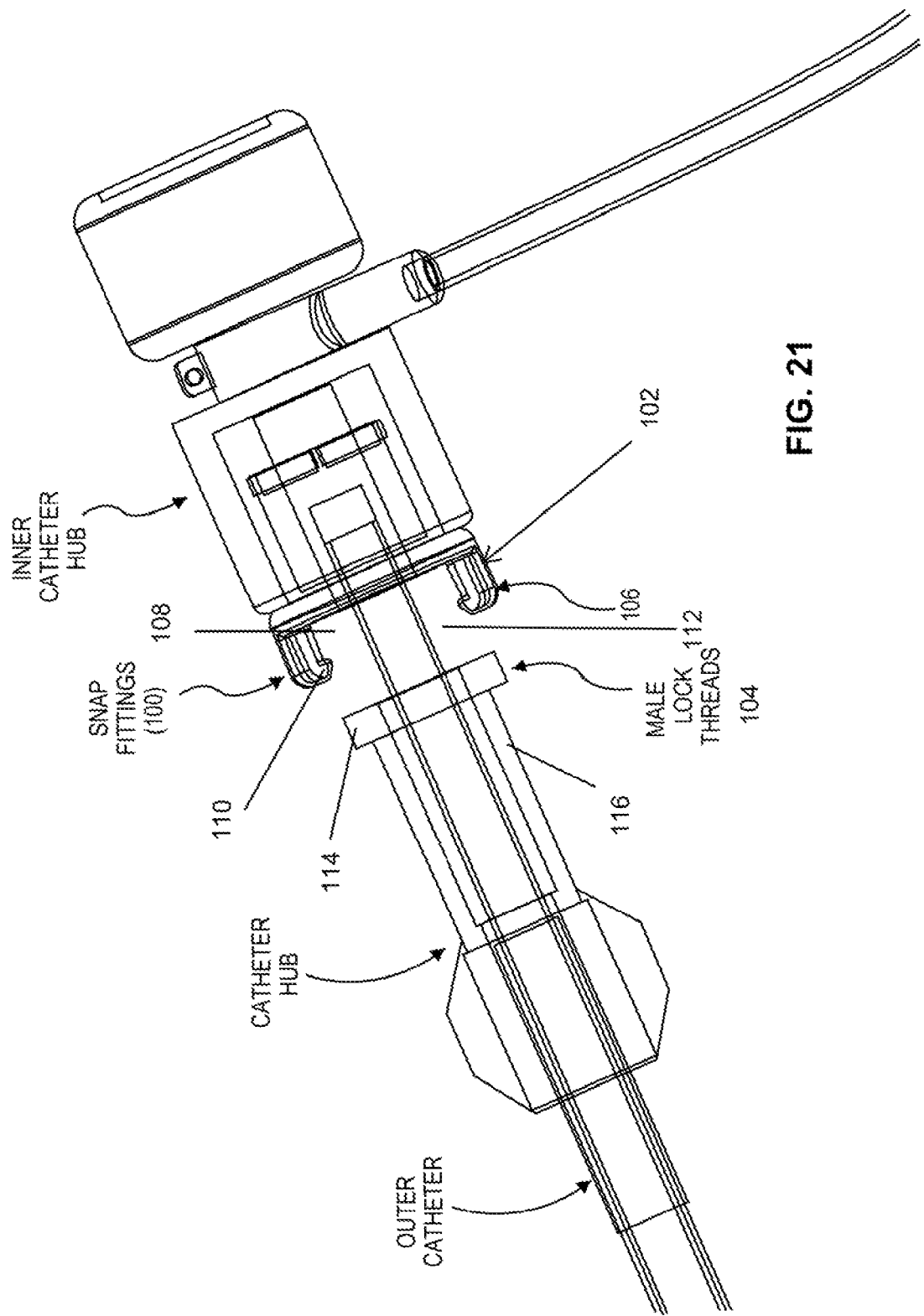
Figure 22:
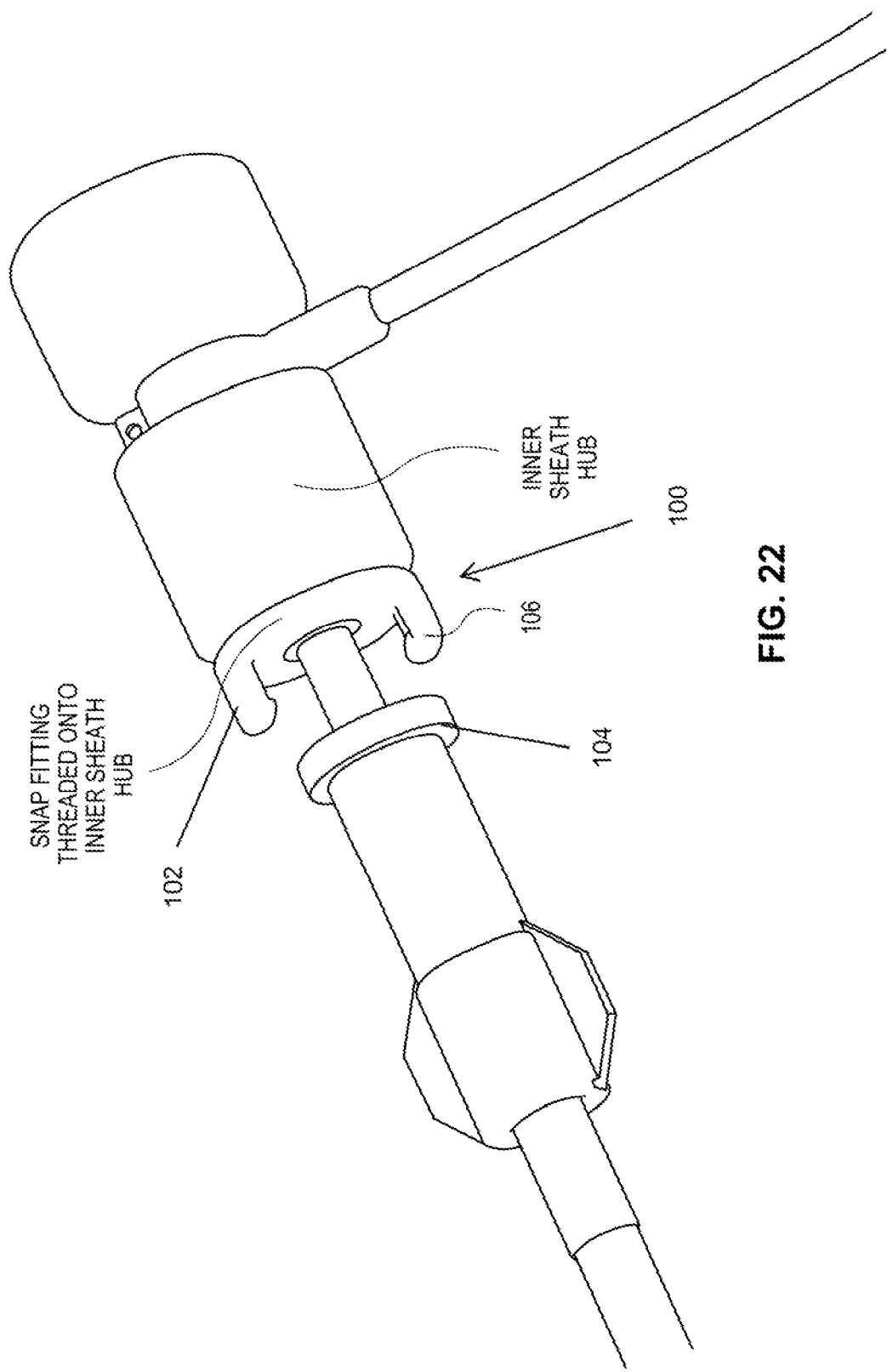

Therefore, it would be advantageous to provide fittings that can more easily be manipulated with one hand, such as a snap fitting, as illustrated in FIGS. 20-22. The snap fitting 100 comprises a female connector 102 and a male connector 104. In some embodiments, the female connector 102 can have a plurality of flexible latch portions 106 that define an opening 112 and enclose a receptacle 108 that is configured to receive the male connector 104. For example, the female connector 102 can have 2, 3, 4 or more latch portions 106. The distal end of each flexible latch portion 106 can include a retaining feature 110 that projects radially inwards and functions to secure the male connector 104 within the receptacle 108. The male connector 104 comprises a distal portion 114 that is configured to fit through the opening 112 and within the receptacle 108. The male connector 104 can also include a narrow stem portion 116 that has a diameter less than the diameter of the opening 112. In some embodiments, the distal portion 114 and/or the latch portions 106 can be tapered towards the outer or inner edge in order to present an angled surface to the opening 112 that can aid in widening the opening 112 by pushing apart the latch portions 106.

These snap fittings 100 can be integrated into the proximal ends of the various components described herein, and well as other components that can be used with the retrieval system. Alternatively, the snap fittings 100 can be made into luer lock adaptors, or other connector adaptors such as screw adaptors, that allow the operator to convert a luer lock fitting, or other fitting, into a snap fitting, as illustrated in FIGS. 20-22. In some embodiments, the device can include an outer catheter with an outer catheter hub and an inner catheter with an inner catheter hub. The female connector 102 of the snap fitting 100 can include a locking feature 118, such as a luer lock fitting, that allows it to reversibly attach to the inner catheter hub. The outer catheter hub can include the male connector 104, which can be integrated into the outer catheter hub as illustrated, or can be reversibly attached as described above for the female connector 102. In some embodiments, all the components are locked together during insertion.

In some embodiments, the proximal gripping portions of the components can include an indicator that identifies which component the operator is gripping, thereby reducing the confusion that can occur in locating the corresponding proximal gripping portion for the desired component. In some embodiments, the gripping portion can include a visual indicator. For example, the different components can have color coded gripping portions, or can be labeled with, for example, an easily read symbol or the name of the component. In some embodiments, the gripping portion can include a tactile indicator that allows the operator to distinguish between the different components without having to look at the gripping portions, which allows the operator to maintain visual focus on more important matters, such as real-time imaging of the retrieval system within the patient provided through fluoroscopy. For example, one component can have a smooth gripping portion, another component can have a rough or knurled gripping portion, and another component can have a dimpled or ridged gripping portion. Each component can have a different tactile pattern to provide tactile contrast between the components.

In some embodiments, the snare handle portion can include snare deployment indicators, such as detents, that allow the operator to easily identify and achieve the different stages of snare deployment described above. For example, the operator can deploy the snare using the snare handle until the snare handle reaches a first indicator, which signifies that the snare is deployed in the first deployment stage. The operator can then further deploy the snare using the snare handle until the snare handle reaches a second indicator, which signifies that the snare is deployed in the second or intermediate deployment stage. Then the operator can further deploy the snare using the snare handle until the snare handle reaches a third indicator, which signifies that the snare is fully deployed. In some embodiments, there is a snare deployment indicator for each stage of snare deployment. In some embodiments, the loop elements of the snare have different configurations in each of the different deployment stages as, for example, described above. For example, deployment indicators can be provided to allow the operator to deploy the snare in stages as described above with respect to FIGS. 1D-1G and FIGS. 1N-1Q. As described above, a deployment stage corresponding to loop elements having an axial configuration can be particularly suited for retrieval of guidewires, leads, and other objects that are positioned transversely with respect to the snare axis. The fully deployed configuration can be particularly suitable for devices that have been designed for retrieval with the snare, such that markers can be used to align the snare with the object to be retrieved. In addition, the fully deployed configuration is particularly suitable for retrieving objects that are located near or proximate the lumen wall.

While described in various embodiments for retrieval of filters and other medical devices and objects, the sheath and snare designs may also be used to retrieve other filter devices, other embolic protection devices, and other objects. For example, filter devices and other devices described in commonly assigned, and concurrently filed U.S. Provisional Patent Application Ser. No. 61/586,661 is incorporated herein by reference in its entirety and for all purposes.

It is understood that this disclosure, in many respects, is only illustrative of the numerous alternative filtering device embodiments of the present invention. Changes may be made in the details, particularly in matters of shape, size, material and arrangement of various filtering device components without exceeding the scope of the various embodiments of the invention. Those skilled in the art will appreciate that the exemplary embodiments and descriptions thereof are merely illustrative of the invention as a whole. While several principles of the invention are made clear in the exemplary embodiments described above, those skilled in the art will appreciate that modifications of the structure, arrangement, proportions, elements, materials and methods of use, may be utilized in the practice of the invention, and otherwise, which are particularly adapted to specific environments and operative requirements without departing from the scope of the invention. In addition, while certain features and elements have been described in connection with particular embodiments, those skilled in the art will appreciate that those features and elements can be combined with the other embodiments disclosed herein.

What is claimed is:

1. A device for retrieving an object from a lumen defined by a lumen wall, the device comprising:
    a sheath configured to fit within the lumen, the sheath having a proximal end and a distal end wherein the sheath includes a flexible distal tip portion that is configured to invert when the object is withdrawn into the sheath; and
    a snare slidably disposed within the sheath, the snare having a shaft with a longitudinal axis, a proximal end and a distal end and a plurality of individual loop elements in connection with the distal end of the shaft, wherein each of the plurality of individual loop elements have a collapsed configuration within the sheath and a plurality of deployed configurations outside the sheath, wherein the plurality of deployed configurations comprises an initially deployed configuration, an intermediate configuration, and a subsequently deployed configuration,
    whereupon the plurality of individual loop elements being initially deployed from the sheath, each of the plurality of individual loop elements are oriented in the initially deployed configuration in a direction substantially 90 degrees to the longitudinal axis and having a first effective diameter,
    whereupon the plurality of individual loop elements being further deployed from the sheath, the plurality of individual loop elements are oriented in the intermediate configuration, wherein the intermediate configuration comprises each of the plurality of individual loop elements being disposed further distally relative to the distal end of the sheath than in the initially deployed configuration;
    whereupon the plurality of individual loop elements being further deployed from the sheath, the plurality of individual loop elements are oriented in the subsequently deployed configuration, wherein the subsequently deployed configuration comprises (a) each of the plurality of individual loop elements having a substantially continuous shape, (b) a portion of each of the plurality of individual loop elements overlaps with at least one portion of another individual loop element, whereby the individual loop elements collectively form a substantially continuous, circumferential and elliptical shape oriented transversely to the longitudinal axis, and (c) each of the plurality of individual loop elements being disposed further proximally relative to the distal end of the sheath than in the intermediate configuration.

2. The device of claim 1 wherein each of the plurality of loop elements includes at least one shape memory wire and one radiopaque wire.

3. The device of claim 2 wherein the shape memory wire is made of a nickel titanium alloy and the radiopaque wire is made of platinum.

4. The device of claim 1 wherein proximal portions of the plurality of loop elements comprise spoke portions that are secured together with a flexible sleeve.

5. The device of claim 1 wherein the object is a filter having a retrieval element and a support member, and wherein an axial reach of the loop elements in another deployed configuration is less than the distance between the retrieval element and the support member.

6. The device of claim 1 wherein each of the sheath and the shaft have a proximal portion, and wherein the proximal portion of the sheath and the proximal portion of the shaft are connected with a snap fitting.

7. The device of claim 1 further comprising an outer sheath, wherein the sheath is disposed within the outer sheath.

8. The device of claim 7 wherein the outer sheath has greater column strength than the sheath.

9. The device of claim 1 wherein the loop elements have a plurality of deployment configurations, and wherein a proximal portion of the shaft includes a plurality of indicators that correspond to the plurality of deployment configurations.

10. The device of claim 9 wherein the plurality of indicators comprise a plurality of detents.

11. The device of claim 1 wherein a proximal portion of the sheath includes a first tactile identifier and a proximal portion of the shaft includes a second tactile identifier, wherein the first tactile identifier is different from the second tactile identifier.

12. The device of claim 1 wherein the plurality of individual loop elements overlap with each other in the subsequently deployed configuration so that outer portions of each individual loop element become portions of the substantially continuous, circumferential and elliptical shape.

13. The device of claim 1 wherein at least a first portion of the deployed snare formed by the plurality of individual loop elements is distal to the distal end of the shaft and a second portion of the deployed snare formed by the plurality of loop elements that is not directly attached to the shaft is proximal to the distal end of the shaft, and wherein the second portion of the plurality of loop elements proximal to the distal end of the shaft is configured to achieve complete circumferential apposition with the lumen wall in another deployed configuration.

14. The device of claim 1 wherein the substantially continuous, circumferential and elliptical shape comprises a major axis and a minor axis, and wherein the major axis of the snare is rotatable to thereby extend a reach of the snare.

15. The device of claim 14 wherein the loop elements are proximally biased.

16. A device for retrieving an object from a lumen, the device comprising:
   a sheath configured to fit within the lumen, the sheath having a proximal end and a distal end; and
   a snare disposed within the sheath, the snare having a shaft with a longitudinal axis, a proximal end and a distal end and a plurality of individual loop elements in connection with the distal end of the shaft, wherein the plurality of individual loop elements has a collapsed configuration within the sheath and a plurality of deployed configurations outside the sheath, wherein each of the plurality of individual loop elements are configured to be deployed through an opening at the distal end of the sheath in an initially deployed configuration, an intermediate configuration, and a subsequently deployed configuration,
   whereupon the plurality of individual loop elements being initially deployed from the sheath, each of the plurality of individual loop elements are oriented in the initially deployed configuration, wherein the initially deployed configuration is oriented substantially 90 degrees with respect to the longitudinal axis,
   whereupon the plurality of individual loop elements being further deployed from the sheath, the plurality of individual loop elements are oriented in the intermediate configuration, wherein the intermediate configuration comprises each of the plurality of individual loop elements being disposed further distally relative to the distal end of the sheath than in the initially deployed configuration;
   whereupon the plurality of individual loop elements being further deployed from the sheath, the plurality of individual loop elements are oriented in the subsequently deployed configuration so that a portion of each individual loop element forms a portion of a substantially elliptical configuration, and wherein a portion of each of the plurality of individual loop element overlaps with at least one portion of another individual loop elements, whereby the plurality of individual loop elements collectively form the substantially elliptical configuration that is substantially transverse to and circumferential to the shaft, and each of the plurality of individual loop elements being disposed further proximally relative to the distal end of the sheath than in the intermediate configuration.

17. The device of claim 16 wherein the individual loop elements overlap with each other when deployed so that external edges of each individual loop element form the portions of the substantially elliptical configuration.

18. The device of claim 17 wherein a major axis of the snare is rotatable to thereby extend a reach of the snare.

19. The device of claim 16 wherein the loop elements are proximally biased.

20. The device of claim 16 wherein the loop elements are proximally biased so that at least a first portion of the plurality of loop elements is distal to the distal end of the shaft and a second portion of the plurality of loop elements not directly attached to the shaft is proximal to the distal end of the shaft.

21. The device of claim 16 wherein at least some of the plurality of individual loop elements comprise one or more preformed crimps that facilitate collapse of the at least some of the plurality of individual loop elements when compressive forces are applied.

22. The device of claim 16 wherein at least some of the plurality of individual loop elements comprise one or more folds that facilitate collapse of the at least some of the plurality of individual loop elements when compressive forces are applied.

* * * * *